(12) United States Patent
Parce et al.

(10) Patent No.: US 7,037,416 B2
(45) Date of Patent: May 2, 2006

(54) METHOD FOR MONITORING FLOW RATE USING FLUORESCENT MARKERS

(75) Inventors: J. Wallace Parce, Palo Alto, CA (US); Claudia B. Jaffe, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 717 days.

(21) Appl. No.: 09/760,009

(22) Filed: Jan. 11, 2001

(65) Prior Publication Data

US 2001/0027918 A1  Oct. 11, 2001

Related U.S. Application Data

(60) Provisional application No. 60/176,094, filed on Jan. 14, 2000.

(51) Int. Cl.
*B01D 59/42* (2006.01)
*B01D 61/58* (2006.01)
*C07K 1/26* (2006.01)

(52) U.S. Cl. .................... 204/451; 204/454; 204/461; 204/601; 204/603

(58) Field of Classification Search ............... 204/451, 204/454, 461, 601, 603
See application file for complete search history.

(56) References Cited

U.S. PATENT DOCUMENTS

| | | | |
|---|---|---|---|
| 4,390,403 A | 6/1983 | Batchelder | |
| 4,908,112 A | 3/1990 | Pace | |
| 5,126,022 A | 6/1992 | Soane et al. | |
| 5,498,392 A | 3/1996 | Wilding et al. | |
| 5,571,410 A | 11/1996 | Swedberg et al. | |
| 5,585,069 A | 12/1996 | Zanzucchi et al. | |
| 5,587,128 A | 12/1996 | Wilding et al. | |
| 5,593,838 A | 1/1997 | Zanzucchi et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,699,157 A | 12/1997 | Parce | |
| 5,750,015 A | 5/1998 | Soane et al. | |
| 5,779,868 A | 7/1998 | Parce et al. | |
| 5,800,690 A | 9/1998 | Chow et al. | |
| 5,842,787 A | 12/1998 | Kopf-Sill et al. | |
| 5,852,495 A | 12/1998 | Parce | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,942,443 A | 8/1999 | Parce et al. | |
| 5,948,227 A | 9/1999 | Dubrow | |
| 5,955,028 A | 9/1999 | Chow | |
| 5,957,579 A | 9/1999 | Kopf-Sill et al. | |
| 5,958,203 A | 9/1999 | Parce et al. | |
| 5,958,694 A | 9/1999 | Nikiforov | |
| 5,959,291 A | 9/1999 | Jensen | |
| 5,964,995 A | 10/1999 | Nikiforov et al. | |
| 5,965,001 A | 10/1999 | Chow et al. | |
| 5,965,410 A | 10/1999 | Chow et al. | |
| 5,972,187 A | 10/1999 | Parce et al. | |
| 5,976,336 A | 11/1999 | Dubrow et al. | |
| 5,989,402 A | 11/1999 | Chow et al. | |
| 6,001,231 A * | 12/1999 | Kopf-Sill | ................ 204/454 |
| 6,004,515 A | 12/1999 | Parce et al. | |
| 6,011,252 A | 1/2000 | Jensen | |
| 6,012,902 A | 1/2000 | Parce | |
| 6,042,710 A | 3/2000 | Dubrow | |
| 6,046,056 A | 4/2000 | Parce et al. | |
| 6,068,752 A | 5/2000 | Dubrow et al. | |
| 6,071,478 A | 6/2000 | Chow | |
| 6,074,725 A | 6/2000 | Kennedy | |
| 6,080,295 A | 6/2000 | Parce et al. | |

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |

(Continued)

OTHER PUBLICATIONS

Cohen, C.B. et al., "A Microchip-Based Enzyme Assay for Protein Kinase A," *Anal. Chem.* (1999) 273:89-97.

Dasgupta, P.K. et al., "Electroosmosis: A Reliable Fluid Propulsion System for Flow Injection Analysis," *Anal. Chem.* (1994) 66:1792-1798.

(Continued)

*Primary Examiner*—Ling-Sui Choi
(74) *Attorney, Agent, or Firm*—Donald R. McKenna; Ann C. Petersen

(57) ABSTRACT

Microfluidic methods, devices, and systems are provided for monitoring and controlling flow rates in response to one or more marker signals. The marker signals are used to provide an indication of flow rate in the various channels of the devices. Signals obtained from the markers are deconvoluted and used in a feedback loop to make flow rate adjustments.

70 Claims, 7 Drawing Sheets

FOREIGN PATENT DOCUMENTS

| WO | WO 99/10735 | 3/1999 |
|---|---|---|
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |
| WO | WO 00/43766 | 7/2000 |
| WO | WO 01/02850 | 1/2001 |
| WO | WO 01/14064 | 3/2001 |
| WO | WO 01/14865 | 3/2001 |

OTHER PUBLICATIONS

Jacobson, S.C. et al., "Fused Quartz Substrates for Microchip Electrophoresis," *Anal. Chem.* (1995) 67:2059-2063.

Manz, A. et al., "Electroosmotic pumping and electrophoretic separations for miniaturized chemical analysis systems," *J. Micromech. Microeng.* (1994) 4:257-265.

Ramsey, J.M. et al., "Microfabricated chemical measurement systems," *Nature Med.* (1995) 1:1093-1096.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow Within a Manifold of Capillaries on a Glass Chip," *Anal. Chem.* (1994) 66:3485-3491.

Sundberg, S. A., "High-throughput and ultra-high-throughput screening: solution—and cell-based approches," *Current Opinions in Biotechnology* 2000, 11:47-53.

\* cited by examiner

Fig. 7A 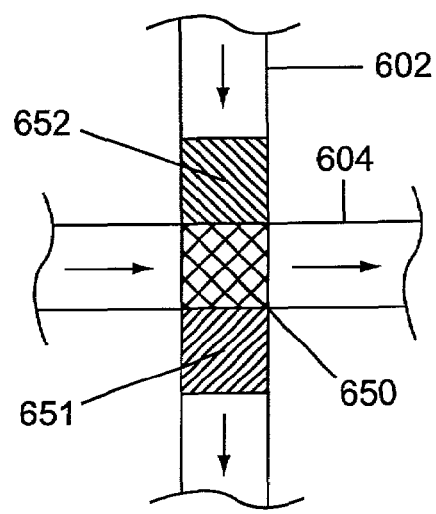 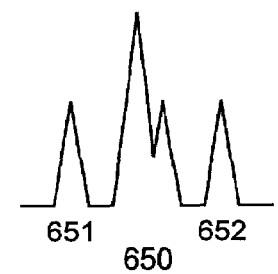
Fig. 7B 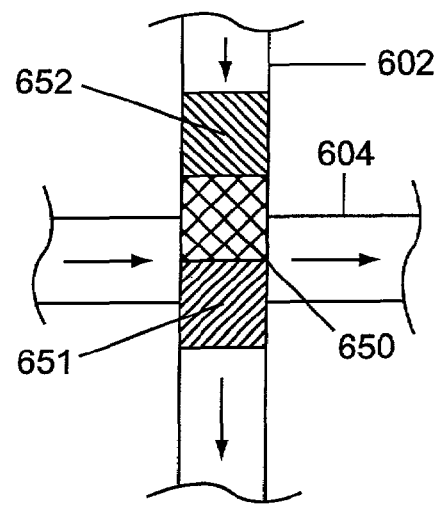 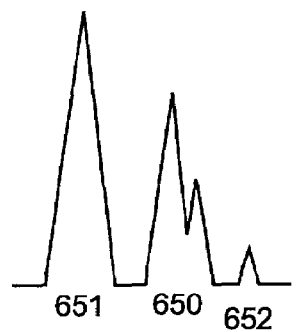
Fig. 7C 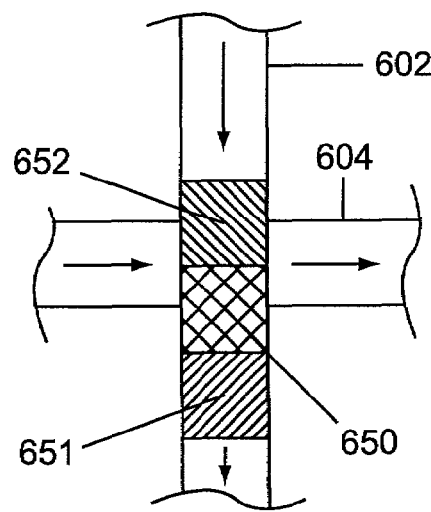 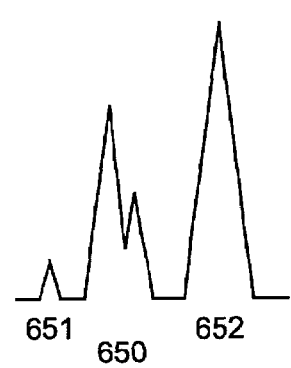

METHOD FOR MONITORING FLOW RATE USING FLUORESCENT MARKERS

CROSS-REFERENCE TO RELATED APPLICATIONS

Pursuant to 35 U.S.C. § 119(e) and any other applicable statute or rule, the present application claims benefit of and priority to U.S. Ser. No. 60/176,094 entitled "Method for Monitoring Flow Rate Using Fluorescent Markers," filed Jan. 14, 2000 by Parce and Jaffe.

BACKGROUND OF THE INVENTION

Biological assays are often performed in high-throughput systems to screen a large number of different compounds for their effect on a biological system, e.g., to screen a plurality of potential enzyme inhibitors. Many of these assays, e.g., enzyme assays, are performed in microfluidic devices as described, e.g., in a number of issued patents and published PCT applications. For example, microfluidic methods of performing biological assays in microfluidic systems have been developed, such as those described by the pioneering applications of Parce et al., "High Throughput Screening Assay Systems in Microscale Fluidic Devices" WO 98/00231 and in Knapp et al., "Closed Loop Biochemical Analyzers" (WO 98/45481).

Materials are typically transported through microfluidic devices by the application of pressure or electrokinetic forces to the channels of the device. The timing of reactions, e.g., in enzymatic reactions, is important for determining reaction kinetics and for making comparisons between various samples. Therefore, a variety of methods have been developed to monitor and control fluid flow in microfluidic systems.

For example, U.S. Pat. No. 5,800,690, by Chow, provides various power supplies, such as time-multiplexed power supplies, to vary the voltage in a microfluidic systems and control fluid movement. Published PCT application WO 98/56956, by Kopf-Sill at al., provides methods of correcting for variable velocity by flowing zwitterions through microfluidic systems. Channel dimensions and configurations have also been varied to provide control over fluid movement in microfluidic channels, such as in U.S. Pat. No. 5,842,787 by Kopf-Sill et al., and in U.S. Ser. No. 60/150, 670 and U.S. Ser. No. 09/645,104, filed Aug. 23, 2000, by Kopf-Sill et al., entitled "Dilutions in High Throughput Systems with a Single Vacuum Source." In "Method and Apparatus for Continuous Liquid Flow in Microscale Channels Using Pressure Injection, Wicking and Electrokinetic Injection," by Alajoki et al., U.S. Ser. No. 09/245,627, filed Feb. 5, 1999, pressure injections and wicking methods for providing continuous flow are described and U.S. Pat. No. 6,001,231, by Kopf-Sill, describes methods of measuring a flow rate in a microfluidic channel.

The present invention provides improved methods and systems for monitoring and controlling flow rates in microfluidic systems. The methods and systems of the present invention provide these features and many others that will be apparent upon complete review of the following disclosure.

SUMMARY OF THE INVENTION

The present invention provides methods, devices, and systems for monitoring flow rates in microfluidic devices using two fluorescent markers. Two or more markers, typically of different electrophoretic mobilities, are used to indicate when changes in the flow rate occur in various channels of the invention. For example, the markers are detected as they elute from, e.g., a separation channel. The peak areas and the retention times are analyzed and compared, e.g., to standard values or to each other, to provide an indication of changes in the flow rate. When flow rate changes are detected, the flow rate is optionally adjusted. The method therefore provides in-line monitoring and control of flow rates, thereby providing flow rate control during long-term operation of the device.

The markers used to monitor and control flow rates in the present invention typically comprise a non-reactive detectable label moiety, e.g., a fluorescent label moiety. The two markers are optionally the same or different. Preferably, the two markers have different electrophoretic mobilities. For example one marker is optionally a charged moiety and the other is optionally a neutral moiety.

In one aspect, a method of monitoring a flow rate of a fluidic material in a microfluidic device is provided. The method comprises flowing a first marker moiety, a second marker moiety, and a fluidic material through a microscale channel. The markers are detected, resulting in signals corresponding to the first marker moiety and the second marker moiety. The fluidic materials or samples are also optionally detected. Each signal has a peak area and a retention time. One or more of the signals are deconvoluted to provide an indication of the flow rate of the fluidic material.

Deconvoluting typically comprises calculating peak areas, heights, and retention times and comparing them to standard values or to each other. Comparison to standard values typically comprises identifying differences between the first marker signal and a first selected standard or between the second marker signal and a second selected standard. For example, identifying differences optionally comprises identifying differences between a peak area for the first or second marker and a standard peak area. In other embodiments, deconvoluting comprises comparing, e.g., the first marker signal and the second marker signal and quantifying the ratio of change between the two, e.g., between the areas or heights. This change provides an indication of whether the flow rate has increased or decreased over time. Alternatively, the deconvolution step comprises identifying differences between the retention time of the first or second marker and a standard retention time. Typically, the first marker and the second marker have different electrophoretic mobilities providing different retention times.

In another aspect, the invention provides methods for modulating the flow rate of fluidic materials within the device. Modulating typically comprises altering, e.g., increasing or decreasing, the flow rate of fluidic material through the channels of the device. The modulation typically occurs in response to the indication of flow rate provided by analysis of the marker signals.

For example, the peak area provides an indication of the amount of marker material that has been introduced into the system, e.g., from a sample well in a microtiter plate. A change in flow rate changes, e.g., the amount of material that is introduced into the system, e.g., through a cross-injection between two microfluidic channels. Therefore, a change in peak area indicates that more or less material is being introduced into the system in a specified time or for a specific sample. The retention time indicates the length of time for a marker to elute from a channel, e.g., a separation channel. Therefore, a change in retention time for a marker of known retention time indicates a change in flow rate, e.g., in an electrokinetically controlled separation channel.

The use of two markers, one flowing in front of a sample and one behind it, is used to indicate the direction of flow rate change, e.g., whether it has increased or decreased. For example, when the marker peak flowing in front of the sample increases and the marker peak flowing behind the sample decreases, it provides an indication that the flow rate has decreased. The ratio of change in peak heights or areas for the bracketing marker peaks provides an indication of the amount and direction of flow rate change.

Typically, the first marker is transported through the device prior to the sample or other fluidic material and the second marker is transported into the device after the sample or fluidic material. Generally, a plurality of samples is transported into and through the device for multiple assays, e.g., screening a library of compounds. The plurality of samples optionally comprises about 96 or more, about 384 or more, or about 1536 or more fluidic samples, e.g., in standard microwell plates. The markers are directed into the system after every sample and/or before every sample. Alternatively, the markers are directed into the device after about every 5, about every 10 or about every 20 samples. This provides for long-term monitoring and modulation of the flow rate within the device.

In a preferred embodiment, the microfluidic devices of the present invention comprise at least two intersecting channels, e.g., a reaction channel and a separation channel. Fluid flow in the reaction channel is typically (although not always) pressure-induced and fluid flow in the separation channel is generally (although not always) electrokinetically-induced. In some embodiments, deconvolution of the marker signals indicates which channel has experienced the change in flow rate.

For example, a reaction channel coupled to a vacuum source that draws samples from a microwell plate draws more fluid from the plate when the pressure increases and less when the pressure decreases. Therefore, the peak area provides an indication of pressure changes, i.e., flow rate changes, in a pressure-controlled reaction channel.

Alternatively, the flow rate in an electrokinetically controlled channel is determined by observation of the retention times of the marker signals. A longer retention time means the marker has taken a longer time to flow through the channel. Therefore, the electrokinetic controller voltages are optionally modulated to maintain an appropriate flow rate in, e.g., the separation channel.

The methods of the present invention are typically carried out in microfluidic systems which typically comprise a microfluidic device and a sample source. A fluid direction system is typically fluidly coupled to the microfluidic device to direct movement of materials, samples, markers, and the like through a plurality of channels. A detection system is typically positioned proximal to the microfluidic device and operably coupled to the fluid direction system, to detect signals, e.g., from fluorescently labeled markers and samples. A computer is also generally included in the system, which computer is operably coupled to the detection system and to the fluid direction system. Software for the computer typically comprises one or more instruction sets, e.g., to instruct the fluid direction system to modulate the flow rate of the fluidic material in response to detected signals, or to calculate peak areas, retention times, and/or flow rates, e.g., for markers and/or samples.

The fluid direction systems of the present invention generally use pressure sources and electrokinetic controllers to induce flow within the channels of the device. A pressure source is optionally a siphon, a vacuum source, a programmable syringe pump, or an electroosmotic pump. The fluid direction system transports fluidic materials and/or markers through the channels of the device.

In some embodiments, the above steps are iteratively repeated such that multiple assays are performed in series in the microfluidic device. A feedback mode provides for detection of the marker signals, deconvolution of the signals, and continual adjustment of the flow rates to a selected value based on the result of deconvolution. Therefore, the invention provides a way to monitor and control flow rate in, e.g., a multichannel microfluidic device, during long-term operation.

BRIEF DESCRIPTION OF THE FIGURES

FIG. 7: Panels A, B, and C depict a sample plug and two markers flowing through the intersection of two microfluidic channels and an example of the corresponding signals obtained when a cross-injection occurs. Panel A presents the ideal situation in which the sample plug is centered over the intersection at the time of injection. However, flow rate changes in the channel can cause the sample plug to be slightly before or slightly past the intersection at the time of the cross-injection. Panel B provides an illustration of what happens in the channel and to the signal under a diminished flow rate and Panel C provides an illustration of the channel and the signal when the flow rate increases.

DETAILED DISCUSSION OF THE INVENTION

Figure 1:
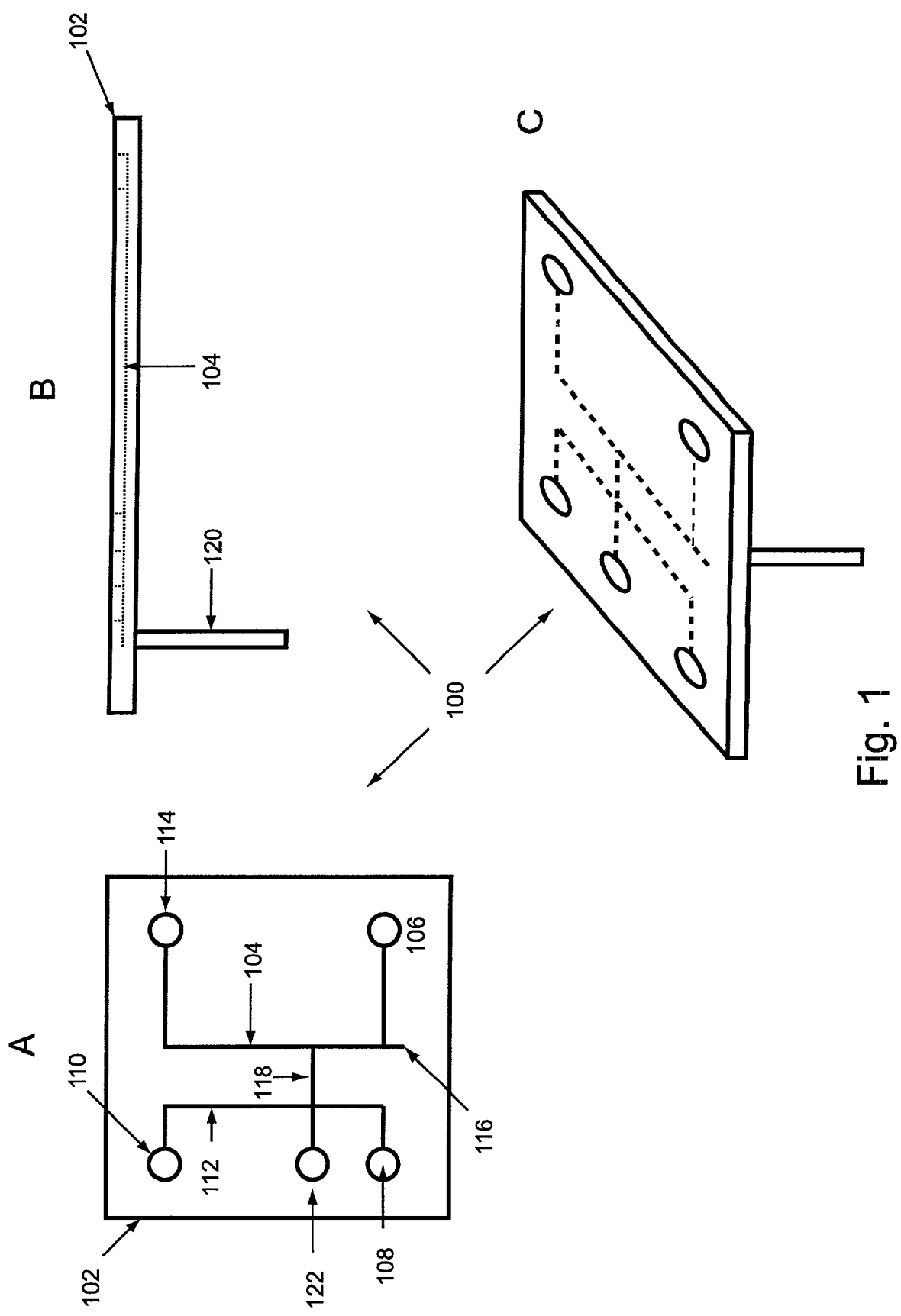
FIG. 1: Panels A, B, and C are schematic drawings of an integrated system of the invention, including a body structure, microfabricated elements, and a pipettor channel.

In many microfluidic device-based assays, a constant flow rate is desired, e.g., to provide steady incubation and reaction times over long-term operation of the device. This allows a plurality of samples, e.g., potential inhibitors or activators, to be assayed and compared. The present invention provides methods of monitoring and modulating flow rates in microfluidic devices, e.g., to provide a substantially continuous flow rate during long-term operation of the device. For example, in the present system, the flow rate is continuously monitored and adjusted as a series of assays is performed. The invention therefore provides an in-line method of monitoring and controlling flow rates during long term operation. As soon as a change in flow rate is detected, the flow rate in the channels is modulated to compensate for the change.

Flow rate monitoring and control are achieved in the present invention by the use of multiple flow rate markers, e.g., non-reactive fluorescent moieties. The markers are flowed through microfluidic devices during an assay to provide an indication of flow rate changes in the assay. For example, when two markers are flowed through a device one typically flows in front of the sample and one behind the sample. When the sample is cross-injected, e.g., into a separation channel, a ratio of the amounts of each of the two markers provides an indication of the amount and level of flow rate change. When flow rate changes are detected, a feedback system is used to modulate the flow rate, e.g., to restore a desired flow rate after a decrease or increase in flow rate has been detected.

The markers are typically non-reactive fluorescent markers that are flowed through the microscale channels with the assay components. The markers are detected, producing a signal for each marker. The signals each have a retention time and an area, which are analyzed and/or compared to provide an indication of flow rate. Two markers are typically used in an assay. For example, one marker is flowed through the system before a sample and one after the sample. The use of two markers allows the timing of a flow rate change to be accurately determined. For example, comparisons between the two marker signals are optionally used to determine whether the flow rate increased or decreased and whether a cross-injection from one channel to another was properly timed.

In addition, the invention provides a method of monitoring flow rates in various channels of microfluidic devices that use both pressure-based and electrokinetic-based flow control. Methods are provided for detecting a flow rate change in a channel and determining the channel in which the flow change has occurred. For example, a change in a marker peak area indicates a flow rate change in the channel from which the marker was introduced. For example, a sample plug is typically cross-injected from a reaction channel into a separation channel. When the flow rate in the reaction channel changes, the amount of markers cross-injected into the separation channel along with the sample plug changes. A comparison of the areas of the two marker peaks indicates whether the flow rate increased or decreased. The flow rate in that channel is then optionally adjusted. Alternatively, a change in a marker peak retention time indicates that the average mobility in an electrokinetically controlled channel has changed. The voltages controlling fluid flow in that channel are optionally varied to compensate for the change, thus providing reproducible retention times, e.g., in an electrophoretic separation channel.

The microfluidic devices used for determining flow rates with multiple markers are described below followed by descriptions of the use of flow rate markers in microfluidic devices, detection and analysis of the markers, and modulation of the flow rate in response to the analysis.

I. Microfluidic Devices for Flowing Multiple Flow Rate Markers

The present invention provides methods of monitoring and modulating flow rates in various channels of microfluidic devices. Various flowing assays are performed in devices of this type, e.g., high throughput assays to test a plurality of potential enzyme inhibitors. In separation-based assays, e.g., assays to determine enzyme kinetics, accurate tracking of compounds is desirable. Sample loading and injecting, e.g., for cross-injections from a pressure driven channel to an electrokinetically driven separation channel, are typically timed and synchronized to provide accurate data acquisition and analysis. The present invention provides methods for in-line monitoring of flow rate changes. With an accurate method of monitoring changes in flow rate, modulations are optionally made to adjust the flow rate, e.g., to a standard or desired value. Therefore, a substantially continuous flow rate is obtained.

The present methods are optionally performed in a variety of devices. In a preferred embodiment, a multi-channel microfluidic device is used. For example, devices are used to carry out reactions or assays, e.g., enzymatic assays, and then to electrokinetically separate products of the reactions or assays, e.g., separation of the product of an enzyme reaction from any unreacted substrate. A variety of devices are optionally configured to control fluid flow using the methods of the present invention.

The devices generally comprise a body structure with microscale channels fabricated therein. For example, a device optionally comprises, e.g., a reaction channel and a separation channel. The reaction and separation channels are fluidly coupled to each other and to various reservoirs or other sources of materials. For example, the channels are optionally intersecting channels. In addition, the devices optionally comprise additional channels and/or regions, e.g., a loading channel, electroosmotic pumping channel, and/or a detection channel region.

Fluidic materials used in the present invention include, but are not limited to, samples, labels, marker moieties, reagents, buffers, and the like. For example, an enzyme assay typically uses a substrate and enzyme, which are combined in the presence of a potential modulator, e.g., an inhibitor or activator. These materials are transported through the various channels of the device using pressure-based flow or electrokinetic flow. For example, pressure induced flow optionally transports materials through the reaction channels of the invention and electrokinetic forces, e.g., electroosmotic or electrophoretic, optionally control the flow of materials in the separation channels. Mixing and reacting of reagents typically occur in the pressure driven channels and separations generally occur in the electrokinetically-controlled channels. For example, pressure driven fluid flow is optionally used to introduce a sample or reagent into a device, e.g., a sipper capillary is used in high throughput systems to sip, e.g., a library of compounds, from a microwell plate. The sample, e.g., an inhibitor, is then optionally combined or mixed, e.g., with enzymes and substrates that are flowing through a reaction channel. The enzymes and substrates react in the presence of the sample or inhibitor to produce, e.g., a product.

In one embodiment, pressure is applied to transport materials and marker moieties into and through the reaction channel and electrokinetic voltages are applied to transport the materials and marker moieties through a separation channel. In a preferred embodiment, the separation channel intersects the reaction channel and materials are cross-injected from the reaction channel into the separation channel. Such a configuration is used, e.g., to perform an enzymatic assay in the reaction channel and electrophoretically separate the products and/or substrates in the separation channel. For example, a plurality of inhibitor samples is optionally sipped under pressure from a microtiter plate into a reaction channel. An enzyme assay is carried out in the reaction channel in the presence of the inhibitor and then the reaction product is separated from the unreacted substrate in the separation channel.

A "reaction channel" of the present invention is typically a channel, channel portion, or region that receives the various reagents, materials, samples, or the like, which are the subject of the desired analysis, or assay. The various reagents of an assay are introduced into a reaction channel, allowed to mix, and then reacted with each other or other reagents. Therefore, the reaction channel of the present invention is optionally an introduction channel or a mixing channel. Although preferably used for fluid based reactions and analyses, it will be readily appreciated that the mixing channel optionally includes immobilized reagents disposed therein, e.g., immobilized on the surface of the channel or upon a solid support disposed within the channel. The mixing channel is typically fluidly connected at one end to a source of at least one reagent or sample. The source is optionally a reservoir, well, sample plate, or microwell plate. Typically a microwell plate is coupled to the device through a sipper capillary or pipettor channel. In addition, the reaction channels typically intersect the separation channels directly or first feed into a loading channel that intersects the separation channel. The loading channel is then used to load or inject the sample into the separation channel, where further analysis is performed.

A "separation channel" is a channel, channel portion, or region in which mixtures of components are separated into their various components. For example, a mixture of proteins as it flows through a separation channel or separation region will be separated into its component proteins. Preferably, the separation channel is a gel filled channel, e.g., a linear polyacrylamide gel filled channel or a polymer solution filled channel, e.g., a polyacrylamide polymer solution or a polydimethylacrylamide/co-acrylic acid polymer, that separates the various components based on molecular weight, wherein each component is eluted from the separation channel with a different retention time. The components are then optionally detected and their molecular weights determined by the retention time. In the present invention, the retention time is analyzed to provide an indication of the average mobility in an electrokinetically controlled channel.

A loading channel is also optionally included in the microfluidic devices and systems in the present invention. A loading channel typically intersects a separation channel and a reaction channel. Materials are electrokinetically loaded from a reaction channel into a loading channel and then electrokinetically injected into a separation channel. For example, a cross-injection from a loading channel into a separation channel injects the volume of fluid at the intersection of the loading channel and the separation channel into the separation channel. The cross-injection is typically timed to inject the sample plug into the separation channel. The markers in the present invention are flowed through the channels before and after the samples and their signals are compared to determine if any flow rate changes have altered the compositions of the injected plug. For example, an alteration in flow rate typically causes less of the sample plug and more of one of the marker moieties to be injected.

Reservoirs, e.g., for storing, discarding, or supplying, samples, reagents, buffers, and the like, are also optionally included in the devices of the present invention. For example, a reservoir for a marker moiety or a sample well is optionally located at one end of a reaction channel for introduction of the sample into the reaction channel. The reservoirs are the locations or wells at which samples, components, reagents and the like, are added into the device for assays to take place. For example, enzymes and substrates are typically flowed through a microfluidic system from reservoirs. Introduction of these elements into the system is carried out as described below.

In one embodiment, the markers and samples of the present invention are sipped from a sample well in a microtiter plate using a sipper capillary. The samples are sipped from the microwell plate into a reaction plate by the application of pressure. For example, a pressure source is optionally coupled to a device to provide a pressure differential, e.g., for sipping marker moieties and potential inhibitors from the microtiter plate. For example, a library of compounds or a plurality of sample compounds at different concentrations are optionally introduced into the systems of the invention from a microwell plate. Other reagents for use in the assay are optionally added from reservoirs or sources described above. Typically, the marker moieties of the invention, e.g., non-reactive fluorophores, are sipped from a microwell plate after each sample, e.g., an inhibitor sample, library member, or the like. Alternatively, the markers are sipped after about every 5 samples, about every 10 samples, or about every 20 samples. The markers are optionally sipped before and after the samples to provide an indication of when in the assay the flow rate changed.

Pressure sources are also optionally applied at the reservoirs of the invention. Typically, reaction channels connect the reservoirs to a pump or other pressure source. For example, a vacuum source may be fluidly coupled to the device at a waste reservoir located at the end of a reaction channel. The vacuum source draws fluid into the reaction channel for mixing or reacting with other reagents. Additionally, the vacuum optionally draws any excess or unused material, e.g., material not loaded into a separation channel, into the waste reservoir to which the vacuum source is fluidly coupled. Alternatively, a positive pressure source is fluidly coupled to a sample well or reservoir at one end of a reaction channel. The pressure then forces the material into and through the reaction channel. Other examples of pressure sources, include, but are not limited to, a siphon, a vacuum source, a programmable syringe pump, or an electroosmotic pump.

Electroosmotic pumps are described by Parce in "Micropump," WO 99/16162. Typically an electroosmotic pump comprises two channels. The pump utilizes electroosmotic pumping of fluid in one channel or region to generate pressure based fluid flow in a connected channel, where the connected channel has substantially no electroosmotic flow generated within it. For example, an electrokinetic controller applies a voltage gradient to one channel to produce electroosmotically-induced pressure within that channel. That pressure is transmitted to a second channel whereupon pressure based flow is achieved. Typically, the channels used for propagating electroosmotic flow have smaller cross-sectional areas than the reaction channels of the invention. These pumps are particularly useful in situations in which application of an electric field to the channel is not desired or where pressure based flow is particularly desirable, e.g., for cell based assays or for introducing, mixing, or reacting materials.

Electrokinetic forces, e.g., high or low voltages, are also optionally applied at the reservoirs to transport materials in the channels. For example, voltage gradients applied across a separation channel are used to move fluid down the channel. An average electrokinetic mobility (or overall flow rate) is achieved depending on the magnitude of voltages applied to the channels. However, the components in the channels typically have different electrokinetic mobilities, e.g., different charges, or different mass/charge ratios. The different mobilities cause the components to flow through the channel at different rates. Consequently, the components are separate as they move through and elute from the channel at different rates.

Detection regions are also included in the present devices. The detection region is optionally a subunit of a channel or it optionally comprises a distinct channel that is fluidly coupled to the plurality of channels in the microfluidic device. The detection region is optionally located at the elution point of the separation channel or region. For example, a detection region located at the most downstream point or end of a separation channel detects the separated components as they exit the separation channel. In other embodiments, the detection region is optionally located at the downstream end of the device just upstream from a waste well.

The detection region or window at which a signal is monitored typically includes a transparent cover allowing visual or optical observation and detection of the assay results, e.g., observation of a calorimetric or fluorometric marker. Examples of suitable detectors are well known to those of skill in the art and are discussed in more detail below.

Figure 3:
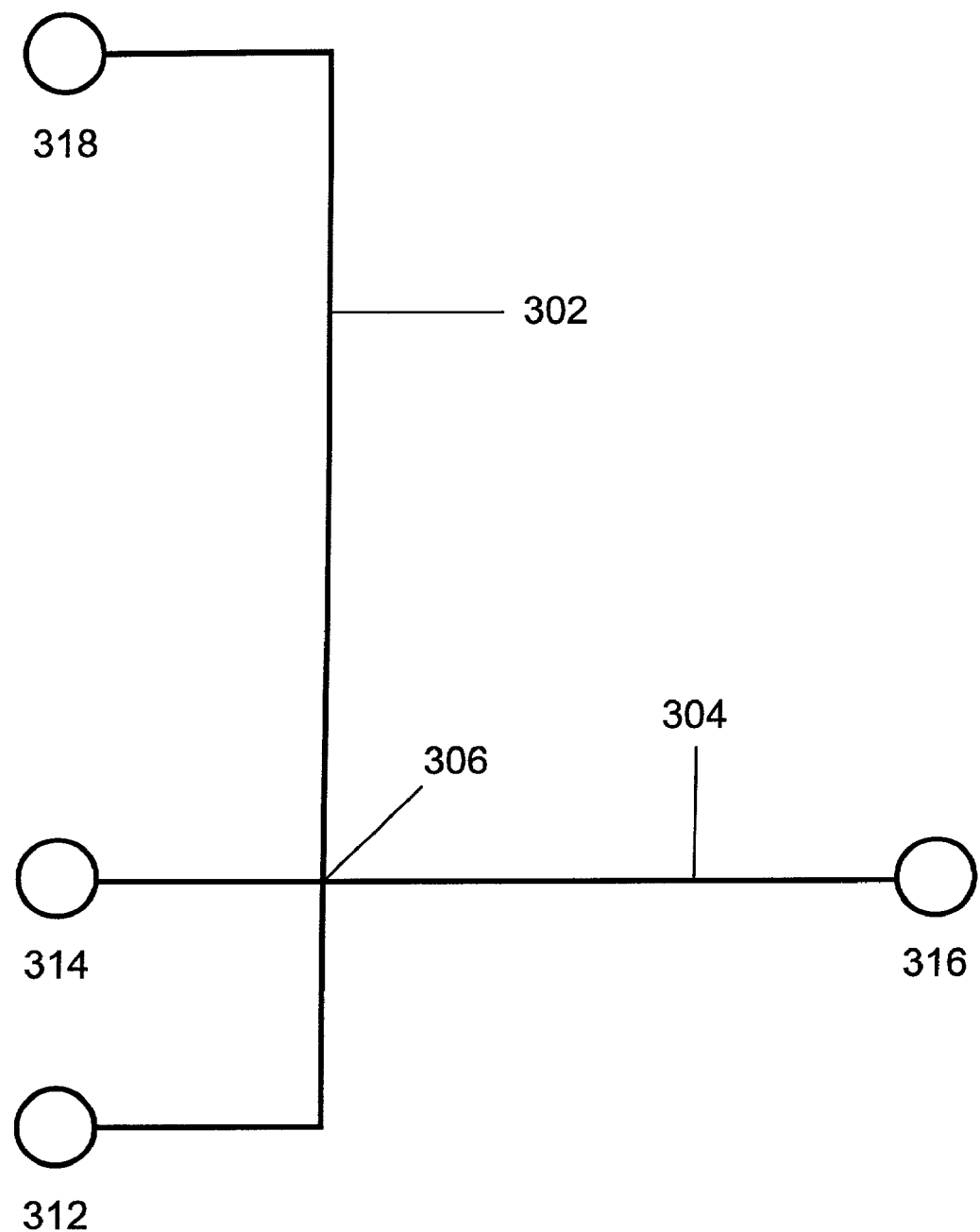
FIG. 3: Schematic illustration of a microfluidic channel configuration useful in practicing the methods of the invention.

One embodiment of a device useful for performing the methods of the present invention is illustrated in FIG. 3. As shown, the system comprises reaction channel 302 and separation channel 304. A sample and a marker moiety or a plurality of samples and a plurality of marker moieties are optionally introduced into reaction channel 302 from a sipper capillary fluidly coupled to reservoir 318. From reservoir 318, a sample is then directed into reaction channel 302. Marker moieties are typically directed into the reaction channel along with the samples. In reaction channel 302 the sample is optionally mixed with a diluent or a buffer or reacted with other reagents, e.g., a substrate and enzyme which are flowed, e.g., continuously, through the device from one or more reservoirs. Since the marker moieties are typically non-reactive marker moieties, they do not typically interfere with the reaction carried out in the reaction channel because they do not react with any of the assay components. Fluid flow in reaction channel 302 is typically controlled by a pressure source, e.g., a pressure source fluidly coupled to either reservoir 318 or waste reservoir 312. For example, a vacuum source is optionally coupled to waste reservoir 312. From reaction channel 302, the sample, e.g., a mixed and/or reacted sample or product is directed via an electrokinetic controller into separation channel 304. The markers are also directed into the separation channel and detected along with the assay products to act as flow indicators. For example, voltages are optionally applied at reservoirs 314 and 316 to cross-inject the material at intersection 306 from reaction channel 302 into separation channel 304. The material typically includes assay product(s) and marker moieties. Preferably, the material at intersection 302 comprises the sample plug, e.g., enzyme and substrate that have reacted in the presence of a sample to produce product, and small amounts of the marker moieties, typically in equal quantities. However, if the flow rate changes in reaction channel 302 then the volume cross-injected into separation channel 304 contain less reacted sample material and more or less of the two marker moieties. A comparison of the amounts of the individual markers indicates the direction of the flow rate change. In separation channel 304, a mixture of components, e.g., proteins, is separated, e.g., by electrophoresis. For example, a substrate, a product, and two marker moieties move through an electrophoretic separation channel at different rates relative to each other. Each component is eluted from the separation channel at a different time, thus providing separation of the components. A detector is optionally positioned proximal to reservoir 316 or proximal to the downstream end of separation channel 304 to detect the components as they elute from separation channel 304. A single detector or multiple detectors are optionally used to detect both the assay product(s) and the marker moieties. When the assay and detection are complete, the sample components are optionally directed to reservoir 316 for disposal or retrieval. Any of the reservoirs, e.g., 314, 316, and 312, are optionally used as waste wells.

Figure 4:
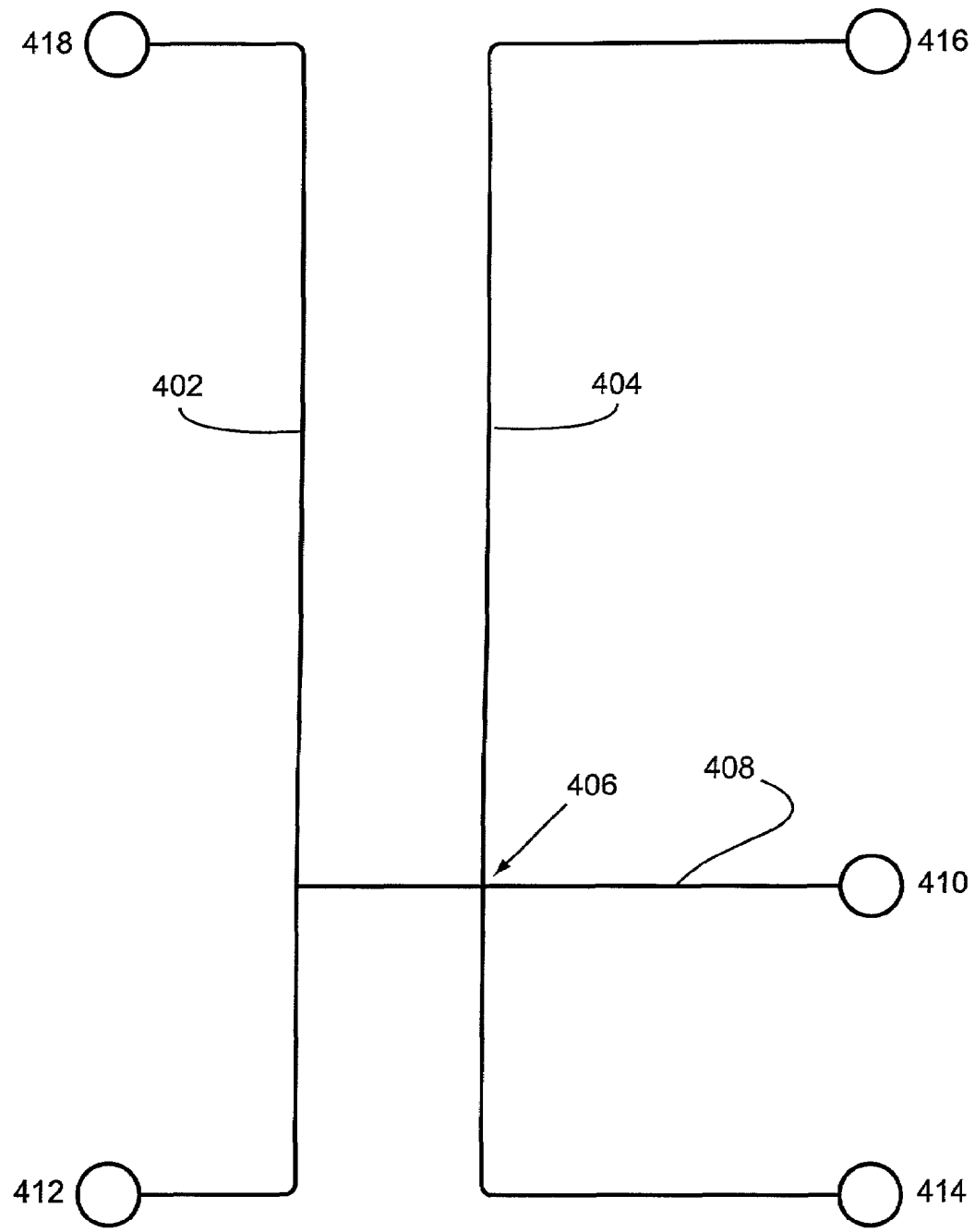
FIG. 4: Schematic illustration of an alternate channel configuration for use with the methods of the present invention.

In an alternate device embodiment, a loading channel is used to direct, e.g., fluidic materials and/or markers, from the reaction channel into the separation channel. FIG. 4 provides a schematic illustration of the channel configuration in a device incorporating a loading channel. The plurality of channels disposed within the device comprises reaction channel 402, separation channel 404, and loading channel 408. A sample and marker moieties are optionally introduced into the device through sample well 418 and are drawn into reaction channel 402 by the application of pressure, e.g., at reservoir 418 or 412. The sample, e.g., an inhibitor, in reaction channel 402 is optionally mixed and/or reacted with other reagents, e.g., an enzyme and substrate, in the presence of the non-reactive marker moieties. The markers and the reagents are optionally introduced into the device through reservoirs 418, 412, and the like. Typically, a microtiter plate or other sample plate is used to introduce the samples and markers into the system and reagents, such as enzymes and substrates, are flowed through the device from reservoirs. The mixed sample and/or reacted product, e.g., leftover substrate and reacted product in an enzyme assay, is then optionally electrokinetically loaded into loading channel 408. For example a voltage difference between reservoir 410 and reservoir 412 or 418 is optionally used to load the sample into loading channel 408. The sample is then injected into separation channel 404. For example, the sample is cross-injected from loading channel 408 into separation channel 404 by a voltage difference between reservoir 410 and reservoir 412. The cross-injection injects the volume of fluid at intersection 406 into separation channel 404. The injection is typically timed to inject a sample plug, e.g., an enzyme and substrate that have reacted in the presence of the sample, into the channel as opposed to injecting enzyme and substrate that have not been contacted by the sample, e.g., an inhibitor, into the channel. If the flow rate in channel 402 or 408 changes, the sample plug may not be centered over the intersection, and thus will not be injected into the separation channel at the cross-injection. For example, an increased flow rate leads to less of the first marker and sample plug being injected and more of the second marker being injected into the separation channel as illustrated in FIG. 7 and described below. The present invention provides methods for monitoring and controlling the flow rate to insure that the timing of the cross-injections remains precise even when changes in flow rate occur.

Once injected into separation channel 404, which is optionally a long serpentine channel to accommodate lengthy separation times, the sample is electrokinetically separated into its components. For example, a mixture of protein fragments produced in a protease reaction are optionally separated into component peptides and amino acids. The markers, which typically have different mobilities from the assay products, are also separated and detected. The sample or products are also detected upon separation. For example, in a enzyme reaction, the product and unconverted substrate are detected and optionally quantified to determine the extent of conversion in the presence of an inhibitor. The marker peaks are optionally used to determine whether flow rate changes occurred in the reaction channel and if so in what direction they occurred. Changes in marker peak area are indicative of changes in the amount of marker injected into the separation channel. A detector is optionally placed proximal to a detection region. Detection regions are optionally located within separation channel 404.

The channel configurations given above are examples of possible combinations. However, it is possible to fabricate additional channels into the device, e.g., to provide pressure-induced flow via an electroosmotic pumping channel or to provide post-separation reactions or labeling. Separation channels are optionally lengthened to accommodate long separation times. In addition, the depths and widths are optionally varied to provide improved separation efficiency. See, e.g., U.S. Ser. No. 60/161710, filed Oct. 27, 1999, and Ser. No. 09/696,749, filed Oct. 24, 2000, both entitled "Pressure Induced Reagent Introduction and Electrophoretic Separation," by Claudia Jaffe, which describe the use of varied channel dimensions for facilitating pressure-induced flow in combination with electrokinetic flow. Various configurations and dimensions are possible to accommodate the fluid flow and flow rate modulation described below.

II. Using Flow Rate Markers in Microfluidic Devices

Fluidic materials are typically flowed through the systems of the present invention using a combination of pressure driven flow and electrokinetically driven flow. As described above, samples are typically introduced into a pressure driven reaction channel and then separated in an electrophoretic separation channel. A cross-injection is typically used to inject a volume of material from the reaction channel into a separation channel. The flow rate in the channel affects what volume of fluid, e.g., a sample plug, a buffer plug, or the marker moieties, is injected into the separation channel. The present invention uses the marker moieties to provide an indication of flow rate changes. Upon detection of a flow rate change, the flow rate is adjusted, e.g., to a standard level such as the initial flow rate, or alternatively, the timing of the cross-injection is altered to compensate for the change in flow rate. The sample is optionally injected into the separation channel directly from the reaction channel or from a loading channel that intersects the reaction channel and the separation channel.

Figure 2:
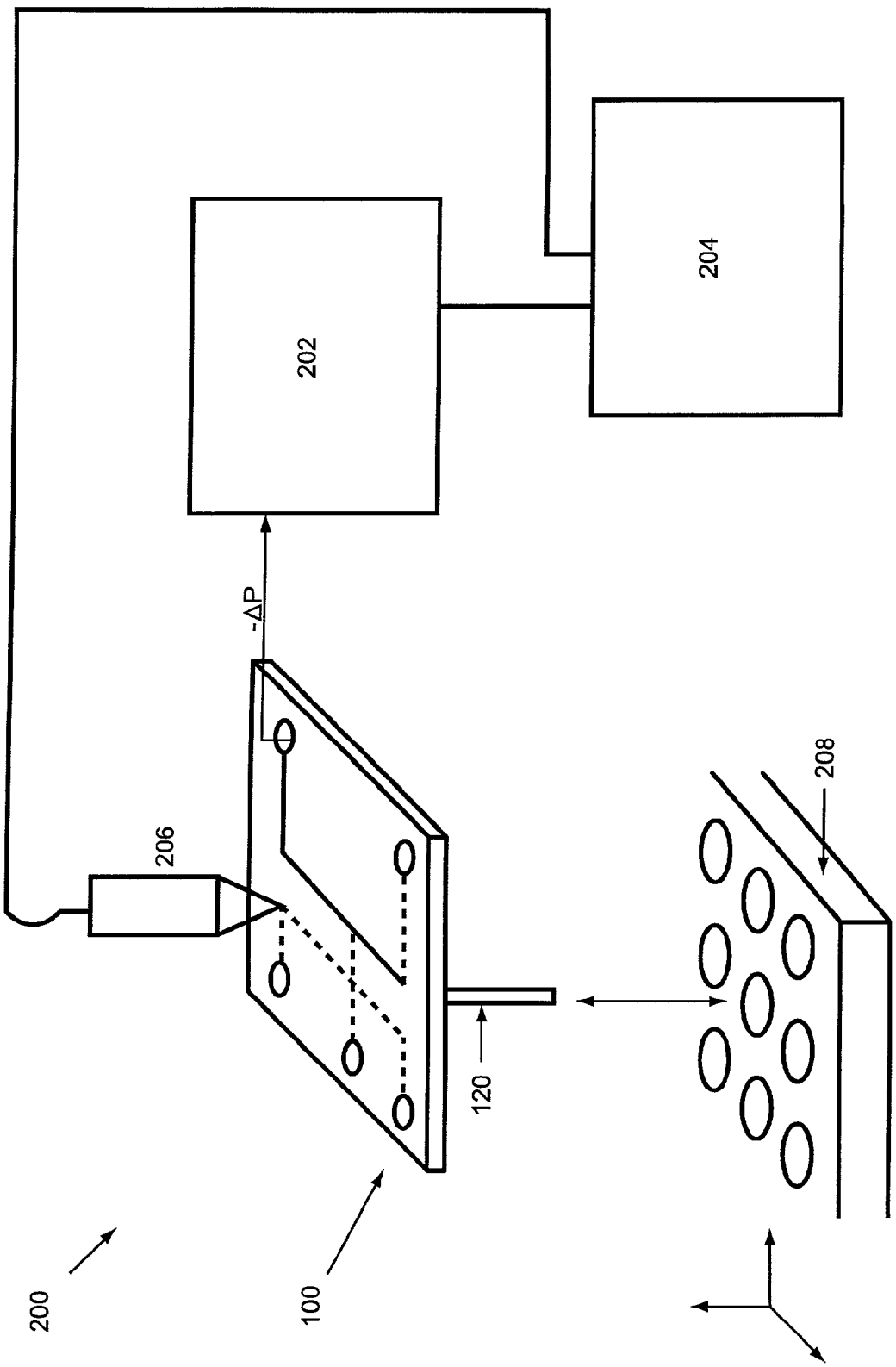
FIG. 2: Schematic drawing of an integrated system of the invention further depicting incorporation of a microwell plate, a computer, detector and a fluid direction system. The integrated system is optionally used with the device or body structure of FIG. 3, 4, or 5, or any other appropriate microfluidic device as described below.

The sample materials are typically added to the reaction channel from a sipper capillary or pipettor channel (as shown in FIGS. 1 and 2) coupled to the reaction channel. Samples are sipped from the sample wells of a microtiter plate, e.g., a 96-well plate, a 384-well plate, a 1536-well plate, or the like. The microwell plates of the present invention optionally comprise a plurality of sample wells, buffer wells and/or marker wells. Samples are sipped one after another, thus performing a series of assays, e.g., in a high throughput format. For example, the samples optionally comprise a library of potential enzyme modulators, e.g., inhibitors or activators, a library of enzyme substrates, e.g., protease substrates, a single compound enzyme inhibitor at multiple concentrations, or the like. The samples are introduced into the device one after the other. A buffer plug is optionally sipped or added after each sample to spatially separate the different samples and to avoid mixing the different samples together, e.g., in the reaction channel. In this manner, a plurality of samples is added to the device in series. The sipper capillary, in this case, is stepped alternately between a buffer well and a sample well. Each sample, after introduction into the system, flows through the channels to be assayed. For example, an assay optionally comprises an enzyme reaction, separation of the reaction products, and detection of the separated products.

The markers of the present invention are used to monitor the flow rate of the fluidic materials, e.g., samples, within the channels. The makers are typically introduced alternately with the samples. For example, a first marker moiety is introduced into the device, then a sample, then a second marker moiety. Alternatively, the markers are introduced into the device after about every five samples, after about every ten samples, about every fifteen samples, or about every twenty samples. This provides for long-term monitoring and modulation of flow rate changes. The markers are optionally sipped before the samples, after the samples, or one is sipped prior to the sample and one is sipped after the sample. The markers are typically contained within sample wells in the same microwell plate as the samples or a different microwell plate. The markers are also optionally contained in the buffer wells or in marker wells of a microwell plate. A robotic sampler is optionally used to step the sipper capillary between the various sample wells of the one or more microwell plates. For example, the capillary optionally sips a first marker moiety, then a sample, then a second marker moiety, then a second sample, then the first marker moiety, and so on.

The markers used in the present invention are flowed through the channels of a microfluidic device with, e.g., the sample materials, substrates, enzymes, modulators, reagents, buffers, and the like. The markers are therefore useful in monitoring the flow rate of the materials in the device.

Figure 5:
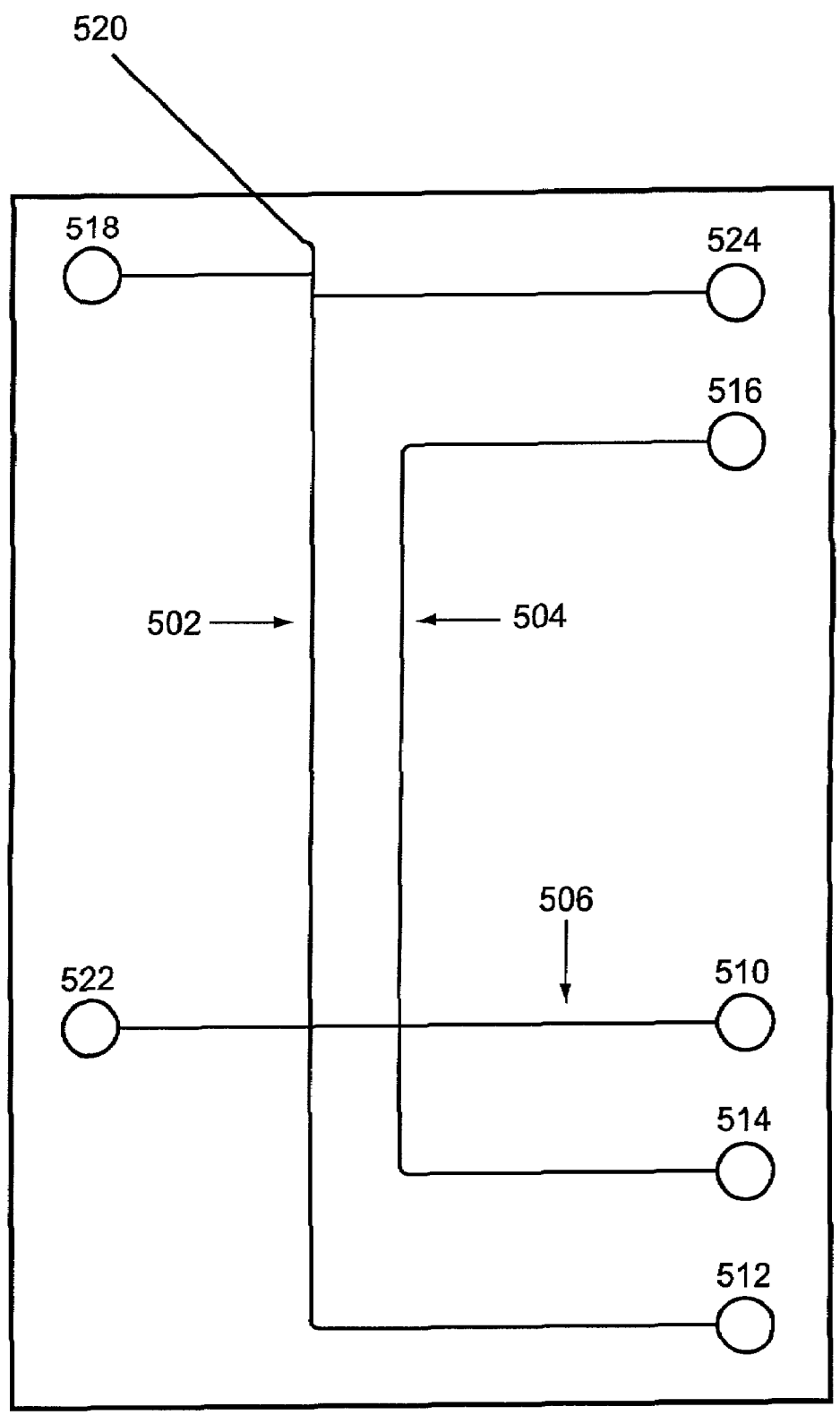
FIG. 5: Schematic illustration of an alternate channel configuration for use with the methods of the present invention.

For example, these methods are optionally implemented in a microfluidic device during performance of an enzyme inhibition assay. For such an assay, a siphon is optionally coupled to a sipper capillary, such as capillary 520 in the device pictured in FIG. 5. FIG. 5 provides an alternate channel configuration for use in the present methods. Capillary 520 is also coupled to a mixing channel, e.g., channel 502, that feeds to two reagent channels, e.g., substrate and enzyme reservoirs such as reservoirs 518 and 524. The two reagents are sucked into the reaction channel while the sipper is alternately stepped through inhibitor or sample wells interspersed with buffer wells. The sipper adds, e.g., the sample to be assayed, the markers for monitoring flow rate, and buffers, to, e.g., the reaction channel. The buffer serves to separate the compounds in time. Marker moieties are optionally spiked into the buffer wells to serve as flow markers.

Figure 6:
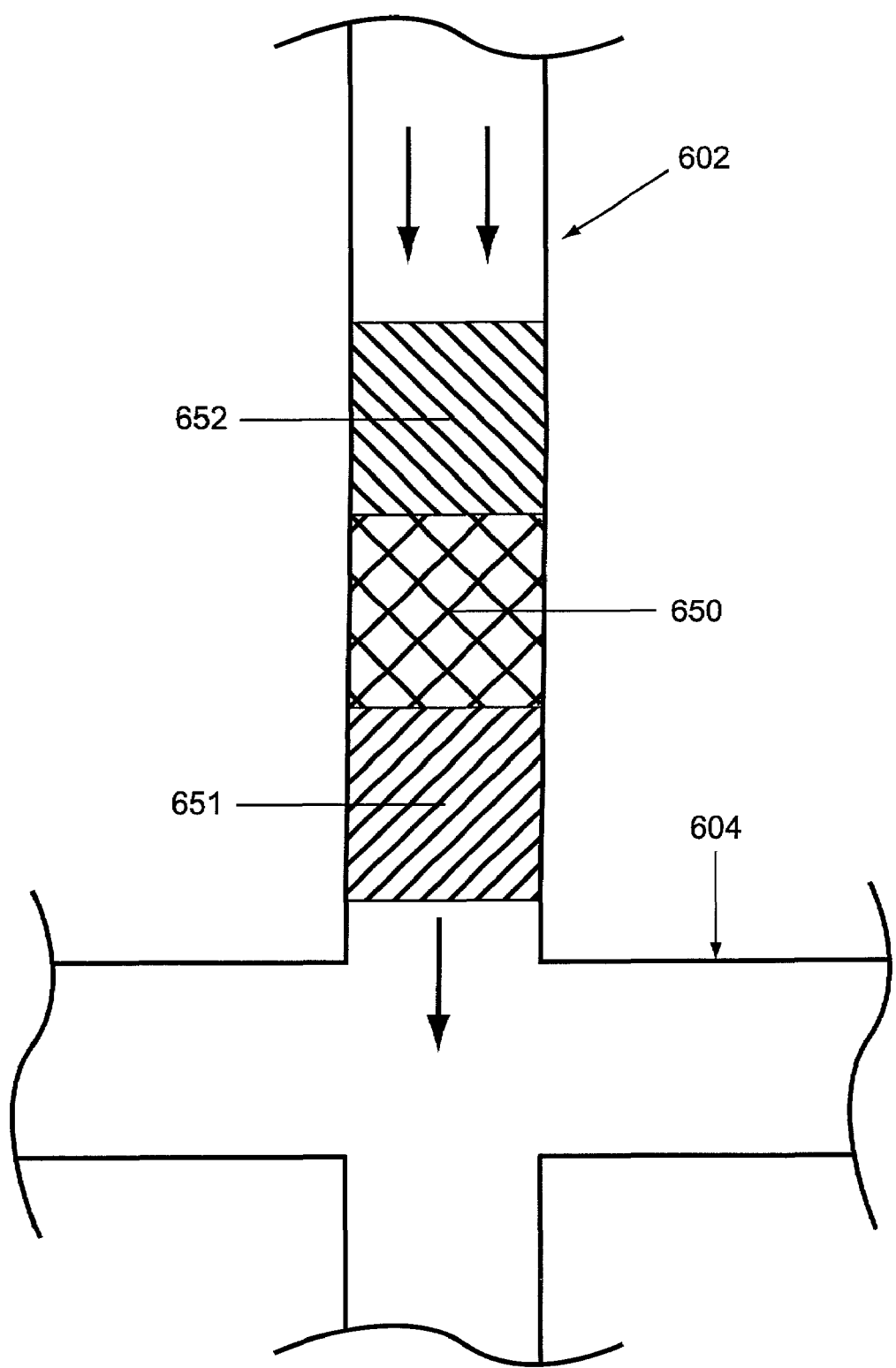
FIG. 6: Schematic illustration of an intersection between two microfluidic channels with a sample plug and two buffers flowing through one of the channels. As the sample materials and markers flow across the intersection a cross-injection is used to inject the sample and markers into the other channel.

Typically two different markers are used, e.g., two markers of different electrophoretic mobility. For example, a neutral and a charged fluorophore are optionally spiked into buffer wells to serve as flow markers. Typically, one marker is introduced before the sample and one marker is introduced after the sample. For example, in a pressure driven reaction channel, one marker flows in front of the sample plug and one marker flows behind the sample plug. See, e.g., FIG. 6. In FIG. 6, sample plug 650 flows through channel 602 in the direction indicated. The first marker, marker 651, flows through the channel before sample plug 650 and the second marker, marker 652, flows through the channel behind the sample. The flow markers are optionally used every time a compound or sample is sipped or after a series of sips, i.e., one injection of markers after about every twenty sample injections. The markers and the sample plug are optionally cross-injected into channel 604, e.g., into a separation channel. Since the reaction channel is typically pressure driven, the markers flow behind or in front of the samples depending on when they were introduced into the system.

Once cross-injected into an electrophoretically controlled channel, e.g., a separation channel, such as channel 604 in FIG. 6, the markers move through the channel based on their electrophoretic mobility. In the separation channel, the two markers are typically separated due to differences in their electrophoretic mobilities. However, the markers do not necessarily have electrophoretic mobilities that bracket those of the sample plug components. For example, the markers optionally have electrophoretic mobilities that are both lower or both higher than the sample components of interest. Alternatively, one marker has an electrophoretic mobility higher than the sample components and one marker has an electrophoretic mobility lower than the sample components. The overall charge of each markers is optionally positive, negative, or neutral and the individual charges can be the same or different but the effective electrokinetic mobilities of the markers, e.g., based on charge to mass ratio, is preferably different so that they are separable in the separation channels of the invention. For example, the label or tag on the marker moieties is optionally the same, e.g., two different rhodamine labeled peptides that have different charge/mass ratios are optionally used.

Typically the markers are fluorescent markers that absorb and emit at wavelengths comparable to those of the other materials of interest, e.g., the substrate and/or products, in the assay being performed. This way, the materials or compounds of interest and the flow markers are all visible with a single detector. Alternatively, the markers absorb and/or emit at different wavelengths from the materials of interest and one detector is used to detect marker signals and a second detector is used to detect the assay products. Furthermore, the markers are typically non-reactive species, such that they do not react with or bind to any of the assay components in the system.

Useful markers include, but are not limited to, fluorescein, fluorescein labeled peptides, fluorescein analogs, BODIPY-fluorescein, arginine, rhodamine-B, rhodamine-A, rhodamine labeled peptides, rhodamine derivatives, and the like. Any two detectable markers with different charge/mass ratios are optionally used. For further information on fluorescent label moieties and fluorescence techniques, see, e.g., *Handbook of Fluorescent Probes and Research Chemicals*, by Richard P. Haugland, Sixth Edition, Molecular Probes, (1996). If fluorescent detection is used, any fluorescent species is optionally used as a marker or tag. Preferably the marker is compatible with the buffer formulation, e.g., it is water soluble and has a good quantum yield at the assay pH. Alternatively, for absorbance detection, chromophores are optionally used as markers. In electrochemical detection, preferred markers comprise electroactive species. UV absorption is also a typical detection method, for which UV absorbers are optionally used as markers. Ideally, the markers used are detectable with the same methods used to detect the analytes or samples of interest, thus simplifying hardware requirements.

Because the markers do not react with the assay components or reactants, they flow unchanged through the channels of the device along with the assay components and reactants. The concentration of markers in each well is known and the retention time of the markers in an electrophoretic separation channel under specified conditions is known. When the specified conditions change, e.g., the flow rate or average electrophoretic mobility in a channel, the marker signal peaks reflect the change by exhibiting different peak areas and/or retention times as compared to known and/or expected values. Upon detection and analysis, this change provides an indication of flow rate that is optionally used to modulate and adjust the channel conditions to maintain a constant or continuous flow rate.

III. Detecting and Analyzing Flow Rate Markers

Detection and analysis of the above markers as they flow through microfluidic channels of the invention with the samples to be assayed provide an indication of the flow rate of the samples. The flow rate is then optionally modulated in a feedback mode to provide a substantially constant flow rate during long-term operation of the device. Therefore, incubation and reaction times and cross-injections can be carefully monitored, controlled, and compared between multiple assays.

Detection

The markers of the present invention are typically detected with the sample materials or compounds of interest, e.g., with a single detector positioned proximal to a detection region. Detectors and detection systems useful for detecting fluorescent marker moieties are described in more detail below. Typically, optical detection is employed to obtain a signal corresponding to each marker moiety, e.g., a label moiety, and each labeled assay component, e.g., sample or compound of interest. For example, in an enzymatic assay, alternately sipping a non-reactive marker before and after the sample of interest produces a fluorescence trace when detected. The trace typically comprises, e.g., four discreet peaks. For example, the peaks include a peak for each marker moiety and a peak for each detected assay component, e.g., a substrate peak and a product peak. Alternatively, the peak or peaks for the detected assay component(s) correspond to one conversion of substrate to product, with two peaks detected for the converted reaction. Alternatively, the assay component peaks correspond to a conversion of one detectable substrate species to multiple products, n, yielding n+1 peaks. Detected components alternatively comprises the separated components of a multicomponent, n, analyte, yielding n detectable peaks or less than n detectable peaks. Typically the detectable assay components result from any permutation of multiple assay components with a minimum of two detectable peaks from which to evaluate the extent of reaction, e.g., via a conversion or separation.

Typically the markers and other materials are detected upon elution from a separation channel wherein each peak has a unique elution time that serves to identify the compound. For example, two different markers having two different electrophoretic mobilities elute from a separation channel at two distinct times. When known or standard markers are used under specified, standard, or known channel conditions, they elute from the column at a known retention time. In addition, each peak has a peak area corresponding to the amount of material detected. In addition, the peaks each have a peak width and a peak height or amplitude. After detection, the retention time, peak area, height, and/or amplitude for each marker are compared and analyzed as described below to provide an indication of the flow rate.

Analysis

The signals obtained by flowing non-reactive markers through the devices of the invention along with sample materials provide an indication of the flow rate of materials in the system. To provide an indication of the flow rate, the signals are analyzed or deconvoluted, e.g., using software comprising instruction sets for deconvoluting signals. "Deconvolution," as used herein, typically involves comparing various signals and identifying specific traits. For example, deconvoluting optionally comprises identifying differences between or comparing two signals, e.g., the signals from the first and second markers. The signals that are typically compared include signals from the marker moieties, specified standards, and assay products. For example, to identify changes in flow rate one or more of the following are optionally compared, contrasted and quantified: marker peak areas, marker peak amplitudes, marker peak widths, marker peak retention times, standard peak areas, standard peak heights, standard retention times, product peak areas, product peak retention times, product peak widths, and product peak amplitudes. In addition, deconvolution optionally comprises calculating flow rates and peak areas, e.g., from the peak width and peak amplitude, e.g., at half maximum height.

In the present invention, deconvolution of the marker signals typically provides peak areas and retention times for each marker signal and compares them to each other or to standard values. A standard value or selected standard typically corresponds to a value, e.g., the area or retention time, for a specified or desired set of conditions, e.g., initial conditions that one desires to maintain throughout a high-throughput assay. For example, in a typical enzyme assay a substrate and enzyme are combined to form a product, e.g., in a reaction channel in the presence of an inhibitor sample. The product and any unreacted substrate are separated, e.g., in a separation channel such as a polyacrylamide gel filled channel. The non-reactive marker moieties of the present invention are typically introduced into the system with the substrate and enzyme by alternately sipping the markers before and after the sample, e.g., an inhibitor or activator sample. Detection in this example typically yields four observable peaks, such as those in FIG. 7. The four peaks comprise one peak for each of two markers, 651 and 652, a peak corresponding to the substrate, and a peak corresponding to the product. The substrate and product peaks are represented in FIG. 7 by sample plug 650, which produces two peaks.

Each marker has a unique electrophoretic mobility. The observed or apparent mobility of any moiety is the vector sum of the electroosmotic mobility and the electrophoretic mobility. The elution or retention time for any species in a given set of conditions for separation is a function of the apparent mobility. The electrophoretic mobility for a species is an inherent property of that species under a given set of conditions; it does not change. However, the apparent mobility may change due to changes in electroosmotic flow, e.g., during the time course of a series of analyses. Typically, anything that causes a change in the solution formulation during the voltage-induced separation, e.g., pH changes, electrodegradation of buffer components, and anything that causes a change in the zeta potential of the capillary walls, e.g., surface adsorption of reaction components or contaminants, incurs a change in electroosmotic flow and consequently apparent electrophoretic mobility and consequently observed retention time or elution time. Any such changes in retention time of the marker moiety indicate an alteration in flow and are optionally compensated for by changes in applied separation voltage.

In addition, each marker peak has an area that corresponds to the amount of marker introduced into the system. The quantitation of the separated components is optionally performed from baseline resolved peaks of the electropherogram, e.g., typically using area under the curve (AUC), peak height, peak width, elution time, peak width at half-maximum height, etc. More typically, AUC is used to quantify the amount of markers.

Typically, a standard or known amount of each marker is added into the buffer well or marker well from which it is sipped. The amount of marker introduced into the system depends on the flow rate or pressure that is drawing the fluid from the well into the system and the sipping or dwell time, i.e., the length of time during which the capillary draws fluid from an individual well. The sipper capillary is inserted into each well, e.g., alternating between marker wells and sample wells, e.g., for a selected length of time. Sample times typically range from 0.05 to about 50 seconds, more preferably from about 0.1 to about 30 seconds. Buffer dwell times range from about 0.5 to about 90 seconds or longer, depending on the throughput demands of the assay. Therefore, the amount of marker introduced after each sample is constant when the flow rate and the timing are constant. At a constant time, the amount of marker materials introduced into the system depends on the flow rate. When the flow rate in the system changes, the amount of fluid drawn into the system from the microwell plate changes. For example, when the pressure applied to the materials in a reaction channel decreases, the flow rate decreases and less material is sipped from the microwell plate. Conversely, when the pressure on the reaction channel increases, the flow rate in the channel increases and more fluid is sampled from the microwell plate. If the amount of marker moiety drawn into a channel changes, then peak area corresponding to that marker changes also. Therefore, a change in marker moiety peak area indicates that the flow rate in the introduction channel has changed. In other embodiments, the markers are introduced from internal reservoirs, e.g., using pressure driven flow. The peak areas are used in the same manner, e.g., to insure that the flow rate has not changed.

Additionally, the combination of two marker peaks, one introduced into the system prior to the sample and one introduced after the sample, provide an indication of the direction of a flow rate change in the pressure driven channels. As seen in FIG. 6, a sample plug of material flows through, e.g., channel 602. Sample plug 650 is bracketed by first marker 651 and second marker 652, which were introduced into the channel before and after the sample. As sample plug 650 passes the intersection of channel 604, it is preferably cross-injected into channel 604. The cross-injection is timed to inject fluid from the intersection when sample plug 650 is centered at the intersection. This is illustrated in FIG. 7, Panel A. Preferably, sample plug 650 is centered at the intersection of the two channels and is injected. Typically, small but substantially equal amounts of markers 651 and 652 are injected with the sample plug, due to some substantially equivalent amount of diffusion and/or dispersion of these markers into sample plug 650. Alternatively, where the sample plug is sufficiently large or the transit time is sufficiently short, no marker material from either marker 651 or 652 is injected into channel 604, due to the inability of the markers to diffuse or disperse the distance to the center portion of sample plug 650 in the time permitted. This technique produces assay component peaks(s) and a peak for each of the two markers, marker 651 and marker 652. In FIG. 7, Panel A, the data comprises peaks corresponding to sample 650, e.g., a product and a substrate peak, and two peaks of substantially equal size corresponding to marker moiety 651 and 652. When the two marker peaks are of equal size, it indicates that a substantially equal amount of each marker was injected into the separation channel. When the two marker peaks are nonexistent or very small, it is an indication that the sample plug was centered over the intersection when the cross-injection occurred and little or substantially no marker materials were injected. When the marker peaks, e.g., the area under the curve, change in relation to each other it is indicative of a flow rate change. A larger leading peak indicates a flow rate decrease and a larger following peak indicates a flow rate increase. These changes in the peak areas of the two markers are due to differing amounts being injected into the separation or loading channel. A comparison of the two indicates in which direction the flow rate has changed. A flow rate decrease means the sample plug does not reach the intersection by the injection time and so more of the leading marker is injected. A flow rate increase means the sample plug has passed the intersection before the injection and more of the following marker is injected.

For example, upon cross-injection into a separation or loading channel, the volume of material at the intersection of two channels is injected from one channel into, e.g., a perpendicular channel. What is contained in the volume injected depends in part on the flow rate of the materials in the pressure driven channel. For example, in FIG. 7B, the volume that is injected into channel 604, when compared to Panel A, comprises more of marker 651 and less sample and less of marker 652. The signals detected show that the area of the peak corresponding to marker 651 has increased and the area corresponding to marker 652 has decreased. This indicates a decrease in flow rate. When the flow rate decreases, the cross-injection occurs before sample plug 650 has reached the center of the intersection and differing amounts of the two markers are introduced into the separation channel. Likewise, when the flow rate increases, the volume of fluid at the cross-section changes and sample plug 650 is not centered on the intersection at the time of the injection. Instead, sample plug 650 has passed the intersection and a greater amount of marker 652 is injected into, e.g., channel 604. This is illustrated in FIG. 7, Panel C. The peaks show a larger area for marker 652 than for marker 651. Therefore, the detected signals indicate that the flow rate has increased and the sample plug has passed the intersection before the cross-injection occurred. When the sample plug is not centered over the cross-section of the two channels, additional product or substrate that may have reacted without being exposed to the sample, e.g., the inhibitor in the sample plug, may be included in the detected sample, thus skewing the results of the assay. Therefore, it is desirable to maintain a constant flow rate to insure precise timing of cross-injections, e.g., into the separation channels and/or loading channels.

In an enzyme assay, for example, two markers are typically introduced into the system along with the substrate and enzyme, which are optionally flowed through the system continuously. The enzyme and substrate react, in the presence of the non-reactive marker moieties, to form one or more products. The substrate, product, and markers are then separated in a separation channel. Typically, one marker elutes before the substrate and product and the other marker elutes after the substrate and product. However, both markers may elute either before or after the substrate, e.g., due to electrophoretic mobilities that differ from the sample components. Differences, e.g., in the peak areas, indicate that the amount of marker injected has changed, i.e., due to flow rate changes the sample plug is not centered on the intersection when an injection is made and so more of one or the other marker is injected instead of the complete sample plug. The percent difference between the areas of the marker peaks indicates the magnitude of the flow rate change and the peak identity, e.g., which peak has increased and which has decreased, e.g., the one sipped before or after the sample, indicates the direction of flow change, i.e., if the flow rate has increased or decreased. For example, a deconvolution of the marker peaks that were sipped before and after a sample indicate whether the flow rate changed before or after the sample was sipped, whether the flow rate increased or decreased, and/or how much the flow rate changed over the course of the assay.

Therefore, any change in the AUC of a marker indicates the magnitude of the flow rate change and the peak identity, e.g., the peak sipped before or after the sample, indicates the direction of flow change. For example, if the marker peak preceding the sample is reduced but the second marker peak sipped following the sample remains the same or is larger, the sample has been loaded into the mouth of the loading channel later than in prior sample introductions. The flow rate has increased in this case. Conversely, if the second marker peak following the sample is reduced but the marker peak preceding the sample remains the same or is larger then the flow rate must have decreased as compared to prior sample introductions. Likewise, if both marker peaks have reduced or increased areas the flow rate has changed and a ratio of some quantitative measure of the marker peaks in comparison to the prior sample introductions indicates the direction of the change in flow. In addition, the analysis provides an indication that a particular sample was not introduced in the desired amount and subsequent data handling and/or calculations can optionally adjust for the different amount of sample used or the different reaction time due to a slower flow rate and longer time in the reaction channel.

In summary, variations in the ratios of the two different markers, i.e., leading and following the sample plug, provide an indication of the variations in flow rates. For example, when the leading marker is present at greater amounts, it indicates a slower flow rate because the sample plug has not had sufficient time to reach the intersection. Conversely, a higher ratio of the second marker indicates a faster flow rate because the sample plug has slightly overshot the injection intersection. By monitoring and comparing these ratios, one can adjust flow rates on the fly to provide an optimal injection profile in accordance with the user's desires. Typically, such monitoring, comparing, and adjustment is carried out by a computer that is appropriately programmed for such analysis and adjustment and operably coupled to the flow controller for the system, as described in greater detail herein.

For example, the flow rate is then optionally adjusted, e.g., in a programmable syringe pump, to compensate for the variations. The adjustment of the flow rate, e.g., back to a standard or desired value, allows a plurality of samples assayed in the device over a long period of time to be properly compared and analyzed. Alternatively, the timing of the cross-injection or the sipping is optionally adjusted to accommodate the changed flow rate.

IV. Modulating Fluid Flow in Response to Analysis of Marker Signals

When a flow rate change is indicated by a change in peak area or amplitude or by a change in retention time, the flow rate in the system is optionally modulated to provide a constant flow rate or to alter the flow rate to a desired value, e.g., to achieve a desired reaction time or throughput rate. For example, when the analysis above indicates that the flow rate in a pressure driven channel has increased, the pressure applied to that channel is decreased. The decrease in pressure allows the flow rate to drop to its original, initial, or desired standard value. Alternatively, the pressure is increased to compensate for a decrease in flow rate. The magnitude of the change in peak area(s) is used to determine the magnitude of the pressure change. In an electrokinetically controlled channel, the flow rate is also optionally adjusted. The voltages on the channels are optionally increased to increase the bulk fluid movement average linear velocity in the channel. Each species still moves with a unique electrophoretic mobility, but the change in voltage imparts a change in electroosmotic mobility and therefore causes an adjustment in the observed velocities of each species. Changes in bulk fluid flow due to voltage changes are sufficient to adjust changes in flow rates in a separation channel and return the separation to a condition in which the individual detectable components elute at a constant, reproducible time. The voltages are optionally decreased to compensate for an increased flow rate in a similar manner.

To obtain flow rate modulations, a fluid direction system is typically used. The fluid direction system is typically operably coupled to one or more of a pressure source and an electrokinetic controller. In addition, the fluid direction system is optionally coupled to the detection system and a computer that deconvolutes the signal peaks to provide information on the flow rate changes. The detection system detects the marker peaks, resulting in signals, e.g., fluorescent signals, and the computer deconvolutes the signals to determine the magnitude and direction of any flow rate changes that have occurred in the system and in which channels the changes have occurred. To perform the deconvolution, the computer typically comprises software which comprises a plurality of instructions sets for performing the analyses described above and for calculating the magnitude of pressure or voltage change that will compensate for the identified flow rate change.

The flow rate change information is transferred to the fluid direction system, which then adjusts the flow rate in the system. For example, the fluid direction system decreases the pressure in a programmable syringe pump or increases the pressure pulled by a vacuum to change the flow rate in a pressure controlled channel, e.g., a reaction channel. Alternatively, the fluid direction system alters the voltages applied to an electrokinetically controlled channel to adjust the flow rate in an electrokinetically-driven channel, e.g., a separation channel. Therefore, the markers are used to provide an indication of the flow rate in a microfluidic system. The inline modulation of the flow rate in response to this indication provides for long-term operation of the system, e.g., in a high-throughput system, at a substantially constant flow rate.

V. Integrated Systems for Monitoring Flow Rates Using Multiple Markers

Although the methods and systems specifically illustrated herein are generally described in terms of the performance of a few or one particular operation, e.g., an enzyme assay, it will be readily appreciated from this disclosure that the flexibility of these methods permits easy integration of additional operations into these systems. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assay and detection operations, electrokinetic or pressure-based injection of components, or the like. In addition, the methods described above are optionally performed in a variety of devices performing a variety of assays, analyses, syntheses, preparations, and the like. The assays given above are examples of possible assays performed using the methods described. However, it is possible to monitor and modulate the flow rate in of a variety of assays and experiments using the methods of the invention. In addition, various devices and channel configurations are possible to accommodate the monitoring methods described herein. Examples of devices and systems suitable for assays using the above methods are described below.

Microfluidic Devices Generally

A variety of microscale systems are optionally adapted to the present invention by incorporating microwell plates, separation channels, enzymes, substrates, marker moieties, separation gels, and the like. Microfluidic devices which can be adapted to the present invention by the addition of a microwell plate or a marker moiety, e.g., rhodamine, fluorescein, or the like, are described in various PCT applications and issued U.S. Patents by the inventors and their coworkers, including U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, and U.S. Pat. No. 5,959,291 (Morten J. Jensen) issued Sep. 28, 1999; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, and WO 99/44217.

For example, pioneering technology providing cell based microscale assays are set forth in U.S. Pat. No. 5,942,443, by Parce et al. "High Throughput Screening Assay Systems in Microscale Fluidic Devices" and, e.g., in Ser. No. 60/128,643 filed Apr. 4, 1999 and Ser. No. 09/510,626 filed Feb. 22, 2000, both entitled "Manipulation of Microparticles In Microfluidic Systems," by Mehta et al. Complete integrated systems with fluid handling, signal detection, sample storage and sample accessing are available. For example, U.S. Pat. 5,942,443 provides pioneering technology for the integration of microfluidics and sample selection and manipulation. Furthermore, additional applications have recently been filed describing improved methods for diluting samples, controlling fluid flow, and performing western type assays, e.g., U.S. Ser. No. 09/641,468 by Wada and Murphy, entitled "Microfluidic Analytic Detection Assays, Devices, and Integrated Systems," filed Aug. 17, 2000; and U.S. Ser. No. 09/645,104 by Kopf-Sill et al., entitled "Dilutions in High Throughput Systems with a Single Vacuum Source," filed Aug. 23, 2000.

In general, enzymes, substrates, modulators, fluorophores, and other components can be flowed in a microscale system by electrokinetic (including either electroosmotic and/or electrophoretic) techniques, and/or using pressure-based flow mechanisms, or combinations thereof. For example pressure based flow is optionally used to flow a protease enzyme, a substrate, and an inhibitor into a main channel for a reaction and then electrophoretic flow control is used to separate the reaction products, e.g., a mixture of peptides and/or amino acids resulting from a proteolytic digestion of a protein. The markers of the present invention are flowed through the channels of the device, e.g., with the protease, substrates, and digestion products, to provide an indication of changes in the flow rate during the assay. When changes are detected, the fluid direction system is used to adjust the flow rate.

Electrokinetic material transport systems or electrokinetic controllers are used in the present invention to provide movement of marker moieties, enzymes, substrates, modulators, and the like, through microfluidic channels. For example, the marker moieties of the present invention are transported through the device, e.g., by electrokinetic material transport, to provide an indication of flow rates within the device. "Electrokinetic material transport systems," as used herein, include systems that transport and direct materials within a microchannel and/or microchamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of proteins, enzymes, peptides, fluorophores, etc. suspended within the fluid. Similarly, the components, e.g., proteins, peptides, amino acids, markers, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis. For example, marker moieties, substrates, and products are electrophoretically separated based on mass/charge ratio in a channel comprising a separation polymer, gel, or matrix, such as a polyacrylamide solution.

Typically, the electrokinetic material transport and direction systems of the invention rely upon the electrophoretic mobility of charged species within the electric field applied to the structure. Such systems are more particularly referred to as electrophoretic material transport systems. For example, in the present system, separation of the marker moieties from the assay products typically occurs by electrophoretic separation. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material that alters the surface charge of the channel.

A variety of electrokinetic controllers and systems which are optionally used in the present invention are described, e.g., in U.S. Pat. No. 5,858,195, by Ramsey issued Jan. 12, 1999, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled products in one or more channels toward a detection region or waste reservoir. Particularly, modulation of the voltages applied at the various reservoirs, such as sources 314 and 316, and the like in FIG. 3, can move and direct fluid flow through the interconnected channel structure of the device. For example, a voltage gradient applied between source 314 and a waste reservoir 316 directs fluid through separation channel 304. In addition, a voltage gradient applied between reservoirs 314 and 316 of FIG. 3 is optionally used to inject material at the intersection 306 into separation channel 304.

The voltage gradients applied at the various reservoirs of the system are also optionally used to control the apparent mobility of species in the channel, e.g., to modulate the electroosmotic flow in response to a flow rate change indicated by a change in marker peak area or retention time. Each species moves in the voltage gradient according to its mass/charge ratio. However, if the voltage gradient is increased, substantially all species increase their apparent electroosmotic mobility as the vector sum of the electroosmotic flow and their unique electrophoretic mobility. The relative flow rates of the species with respect to each other are maintained by appropriate adjustment of the applied field to compensate for changes in the electroosmotic mobility, e.g., during the time course of a series of separations.

Other methods of transport are also available for situations in which electrokinetic methods are not desirable. For example, sample introduction and reaction are best carried out in a pressure-based system to avoid electrokinetic biasing during sample mixing and high throughput systems typically use pressure induced sample introduction. Pressure based flow is also desirable in systems in which electrokinetic transport is also used. For example, pressure based flow is optionally used for introducing and reacting reagents in a system in which the products are electrophoretically separated. In the present system, pressure based flow is optionally used to introduce and react the various reagents, e.g., an enzyme and a substrate, and electrophoretic flow control is typically used to separate the products of the assay from the flow indicator markers.

Pressure is optionally applied to microscale elements, e.g., to a channel, region, or reservoir, to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe, or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In some embodiments, a vacuum source is applied to a reservoir or well at one end of a channel to draw a fluidic material through the channel. For example, a vacuum source is optionally placed at a reservoir in the present devices for drawing fluid into a channel, e.g., a vacuum source at reservoir 412 in FIG. 4 applies a pressure to main channel 402, thus drawing fluid into main channel 402, e.g., from a microwell plate fluidly coupled to main channel 402 at reservoir 418. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces are also optionally used to provide fluid pressure for continuous fluid flow of materials such as enzymes, substrates, modulators, or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure. The capillary forces are optionally used in conjunction with the electrokinetic or pressure-based flow in the present invention. The capillary action pulls material through a channel. For example a wick is optionally added to, e.g., main channel 402, to aid fluid flow by drawing samples from a microwell plate into a sipper capillary coupled to main channel 402. Any changes in flow rate due to the addition or removal of a wick are optionally monitored and adjusted by the methods described above.

Mechanisms for reducing adsorption of materials during fluid-based flow are described in U.S. Ser. No. 09/310,027, "PREVENTION OF SURFACE ADSORPTION IN MICROCHANNELS BY APPLICATION OF ELECTRIC CURRENT DURING PRESSUREINDUCED FLOW" filed May 11, 2000 by Parce et al. In brief, adsorption of components, proteins, enzymes, markers and other materials to channel walls or other microscale components during pressure-based flow can be reduced by applying an electric field such as an alternating current to the material during flow. For example, these mechanisms are optionally used in main channel 302 of FIG. 3 to maintain a continuous flow assay. Alternatively, flow rate changes due to adsorption are detected and the flow rate is adjusted by a change in pressure or voltage.

Mechanisms for focusing labeling reagents, enzymes, modulators, and other components into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al. U.S. Ser. No. 09/569,747, filed May 11, 2000. In brief, sample materials are focused into the center of a channel by forcing fluid flow from opposing side channels into the main channel comprising the cells, or by other fluid manipulations. Any changes in the flow rate due to this method of modulation are also optionally compensated for using the methods of the present invention.

In an alternate embodiment, microfluidic systems can be incorporated into centrifuge rotor devices, which are spun in a centrifuge. Fluids and particles travel through the device due to gravitational and centripetal/centrifugal pressure forces.

In addition to transport through the microfluidic system, the invention also provides for introduction of samples, markers, or other reagents, e.g., enzymes, proteins, substrates, modulators, and the like, into the microfluidic system.

Sources of Assay Components and Integration With Microfluidic Formats

Reservoirs or wells are provided in the present invention as sources of samples, reagents, enzymes, substrates, buffers, marker moieties, and the like. Such wells include, e.g., reservoirs 418, 416, 414, and 412 in FIG. 4. For example, a sample is optionally introduced into the device through reservoir 418. The source is optionally coupled to a microwell plate through a pipettor channel as described below and shown in FIGS. 1 and 2. In the present invention, the markers are typically added to the system from a microwell plate fluidly coupled to a reservoir and reaction channel through a pipettor channel or sipper capillary.

Sources of samples, mixtures of components, and reagents, e.g., enzymes, substrates, labeling reagents, and the like, are fluidly coupled to the microchannels noted herein in any of a variety of ways. In particular, those systems comprising sources of materials set forth in Knapp et al. "Closed Loop Biochemical Analyzers" (WO 98/45481) and Parce et al. "High Throughput Screening Assay Systems in Microscale Fluidic Devices" WO 98/00231 and, e.g., in Ser. No. 90/510,626 filed Feb. 22, 2000, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others. In the present invention a microwell plate is a typical source of samples and markers.

For example, the source of a sample, marker, or buffer can be a microwell plate external to the body structure, having, e.g., at least one well with the selected sample, e.g., a potential enzyme inhibitor. For example, a microwell plate containing a plurality of potential inhibitors is optionally coupled to a pipettor channel as shown in FIGS. 1 and 2. The various inhibitors are drawn from the microwell plate into the pipettor channel and then into the microfluidic device, e.g., into main channel 104. In main channel 104 or another channel of the microfluidic device, the inhibitor sample is optionally tested to determine, e.g., activity and/or kinetic rate constants. To accommodate the flow rate monitoring of the above methods, marker wells are included in the microwell plate and alternately sampled such that a marker is sipped after each sample, or after about every 5 samples, about every 10 samples, about every 20 samples, etc.

Alternative sources include a well disposed on the surface of the body structure comprising the sample, component, or reagent, a reservoir disposed within the body structure comprising the sample, component, mixture of components, or reagent; a container external to the body structure comprising at least one compartment comprising the sample, component, or reagent, or a solid phase structure comprising the sample or reagent in lyophilized or otherwise dried form.

For example, enzymes and substrates are optionally contained in surface wells of the device. In some embodiments, voltage or pressure is used to periodically introduce a marker component, e.g., into the main channel, e.g., after about every 5 or 10 samples, from an internal well or reservoir.

A loading channel region is optionally fluidly coupled to a pipettor channel with a port external to the body structure. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic systems of the invention optionally include a very wide variety of storage elements for storing samples and reagents to be assessed. These include well plates, matrices, membranes and the like. The reagents, e.g., marker moieties, are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system. Such reagents include, but are not limited to, marker moieties, e.g., fluorophores, modulators, e.g., inhibitors or activators, enzymes, substrates, and the like.

The above devices, systems, features, and components are used in the integrated systems described below, e.g., to perform enzyme assays, to separate mixtures of products, and the like.

Instrumentation

In the present invention, materials such as enzymes, proteins, antibodies, peptides, polypeptides, amino acids, marker moieties, and the like are optionally monitored and/or detected to detect the presence of a product of interest, to determine an activity or concentration, monitor a flow rate, or the like. For example, in an enzyme assay, the amount of inhibition is determined by analysis of the amount of product formed in the assay, e.g., in relation to the amount of unreacted substrate. Kinetic rate constants are also optionally determined by the analysis of the products formed in the assay. The marker signals are detected and analyzed to provide flow rate information that is used to instruct the fluid direction system to modulate flow rate or to alter incubation and/or reaction times as described above. Furthermore, depending on the label signal measurements, decisions are optionally made regarding subsequent fluidic operations, e.g., whether to assay a particular component or inhibitor in detail to determine, e.g., kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Fluid Direction System

A variety of controlling instrumentation is optionally utilized in conjunction with the microfluidic devices described above, for controlling the transport and direction of fluidic materials and/or materials within the devices of the present invention, e.g., by pressure-based or electrokinetic control. For example electrophoretic control systems are used to transport and separate reaction products in a separation channel region.

In the present system, the fluid direction system controls the transport, flow and/or movement of a sample through the microfluidic device. For example, the fluid direction system optionally directs the movement of the sample through a reaction channel, in which the sample is mixed and reacted with other reagents, e.g., in a protease assay. It optionally directs movement of a sample, an enzyme, and a substrate, e.g., an inhibitor, a protease, and a protein, into a reaction channel. The fluid direction system also transports marker moieties through the reaction channel with the assay components. Other reagents are also optionally added, e.g., buffers, salts, diluents, and the like. The reagents mix and/or react in the main channel, e.g., in the presence of the non-reactive marker moieties. The fluid direction system also optionally directs the transport of the assay products and markers into a separation channel or channel region in which the markers are separated from the assay products. The marker signal information is analyzed as described above and then the fluid direction system responds to this information by adjusting or modulating the flow rate.

For example, in many cases, fluid transport and direction are controlled, in whole or in part, using pressure based flow systems that incorporate external or internal pressure sources to drive fluid flow. For example, samples are optionally introduced into the system using a pressure based flow control, e.g., a siphon fluidly coupled to a sipper capillary.

The pressure sources are also optionally adjusted to control the flow rate, e.g., to maintain a constant flow rate over long-term operation of the system. For example, if the flow rate in the channel changes due to, e.g., fluctuations in the applied pressure or adhesion, the fluid direction system increases or decreases the applied pressure in response to the change, e.g., to maintain a substantially constant flow rate.

Internal pressure sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999 by Chow and Parce, entitled "Devices, Systems and Methods for Time Domain Multiplexing of Reagents".

Alternatively, electrokinetic controllers are used to apply voltage gradients across channel systems, thus transporting components, e.g., charged components through the channels. For example, enzyme assay products are typically separated electrophoretically using electrokinetic controllers to control the voltages applied to the separation channel. The voltages are also optionally increased or decreased to compensate for average electrokinetic mobility changes in the channel as described above.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection System

The devices herein optionally include signal detectors, e.g., which detect fluorescence, phosphorescence, radioactivity, pH, charge, absorbance, luminescence, temperature, magnetism, color, electrochemical, or the like. Fluorescent detection is especially preferred. For example, the markers used to monitor flow rates according to the above methods are typically fluorescent markers. However, other non-reactive detectable markers are optionally used, e.g., markers based on the above-mentioned detection mechanisms. For example, phosphorescent, radioactive, luminescent, colored, ultraviolet, electroactive, and magnetic makers are optionally used. To simplify hardware requirements a single detector is preferably used to detect both markers and analytes or samples. In this case, the markers are chosen to have the same optical or other detectable properties as the analytes or samples of interest. In addition, the assay components are optionally detected using fluorescent detection or one of the above methods. A single detector is optionally used if both the markers and the assay components comprise, e.g., fluorescently labeled moieties. Alternatively, multiple detectors are used to detect the markers and assay components, e.g., to detect fluorescent marker moieties and radioactive assay components.

The detector(s) typically monitors one or a plurality of signals from downstream of the separation region in which the products of interest, e.g., a substrate, product and two markers, have optionally been separated. For example, the detector optionally monitors an optical signal that corresponds to a labeled marker. In another embodiment, the detector monitors a plurality of optical signals, which correspond in position to various separated components, e.g., polypeptides that have been separated by weight.

Substrates, products, marker moieties, or other components which emit a detectable signal are optionally flowed through a detection region of the invention. For example, the labeled markers of the present invention emit a detectable fluorescent signal. A detector is placed proximal to the detection region and the labeled components are detected as they flow past the detector. The signal obtained is used to obtain, e.g., flow rate, concentration, and kinetic data. Alternatively, the detector can move relative to the device to determine the position of a protein, peptide, or the like (or, the detector can simultaneously monitor a number of spatial positions corresponding to different channel regions, e.g., as in a CCD array). In this embodiment, the flow rate methods described above provide flow rate information for each channel in which a marker is detected.

The detector optionally includes or is operably linked to a computer, e.g., which has software for converting detector signal information into assay result information, e.g., molecular weight based on retention time or elution time, concentration of a component, inhibition rate constants, activation rate constants, flow rate, flow rate changes, or the like. In addition, sample signals are optionally calibrated, e.g., by calibrating the microfluidic system by monitoring a signal from a known source.

A microfluidic system also optionally employs multiple different detection systems for monitoring the output of the system. Detection systems of the present invention are used to detect and monitor the materials in a particular channel region (or other detection region). Once detected, the flow rate and velocity of cells in the channels is also optionally measured and controlled as described above.

Typically, the detector in the present invention is an optical detector, e.g., a fluorescence detector that detects fluorescent marker moieties. Optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials' spectral characteristics. In preferred aspects, the detector measures an amount of light emitted from the material, such as from a fluorescent material, e.g., a marker moiety. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as the marker moieties used to monitor flow rates in the present invention, the detector typically includes a light source which produces light at an appropriate wavelength for activating the fluorescent material, as well as optics for directing the light source through the detection window to the product contained in the channel or chamber. The light source is optionally any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. For example, the computer calculates an appropriate flow rate adjustment based on signal information from the detection system and instructs the fluid direction system to change the applied pressure at one or more ports or to change the voltage applied across a particular channel. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport enzymes, substrates, markers, and samples into a reaction channel, products of the enzymatic reaction and the markers into a separation channel, and any other movement necessary to perform the assay of interest.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like. For example, the computer optionally directs the fluid direction to increase or decrease the pressure in a pipettor channel to draw more sample material into the system from a microwell plate after a decrease in flow rate has been detected.

To interpret the data, the computer typically includes software for deconvolution of the signal or signals from the detection system. For example, deconvolution of the data provides flow rates and flow rate comparisons to indicate when a change in flow rate has occurred. Molecular weights and concentrations of the various assay components are also optionally determined by one or more software instruction sets. In addition, instruction sets are optionally included for deconvoluting the data as described in WO 98/56956 and U.S. Ser. No. 09/609,030, entitled "MICROFLUIDIC SYSTEMS AND METHODS FOR DETERMINING MODULATOR KINETICS" filed Jun. 30, 2000, to obtain kinetic rate constants.

Example Integrated System

FIG. 1, Panels A, B, and C and FIG. 2 provide additional details regarding example integrated systems that are optionally used to practice the methods herein. As shown, body structure 102 has main channel 104 disposed therein. For example, an inhibitor sample and markers are optionally flowed from pipettor channel 120 towards reservoir 114, e.g., by applying a vacuum at reservoir 114 (or another point in the system) or by applying appropriate voltage gradients. Alternatively, a vacuum is applied at reservoirs 106, 108, 112 or through pipettor channel 120. Enzymes and substrates are optionally flowed into main channel 104 from reservoirs 106. The enzymes and substrates react in main channel 104 and produce assay products. The non-reactive marker moieties travel through main channel 104 but do not react with the other components. The components of the reaction and the markers are typically separated in a separation region or channel. A separation channel region is optionally included within main channel 104 or as an additional channel. In the channel configuration pictured, the assay products and marker moieties are then flowed through main channel 104 toward loading channel 118. The materials are typically electrokinetically loaded into loading channel 118, e.g., by applying a voltage gradient between reservoirs 114 and 122. A voltage gradient between reservoirs 108 and 110 then injects the volume of material at the intersection of loading channel 118 and separation channel 112 into separation channel 112. Although described in terms of pressure based flow in main channel 104 and electrokinetic flow in separation channel 112, flow in the system is optionally performed by modulating fluid pressure, or by electrokinetic approaches as described (or both). The arrangement of channels depicted in FIG. 1 is only one possible arrangement out of many which are appropriate and available for use in the present invention.

Samples and materials are optionally flowed from the enumerated wells or from a source external to the body structure. As depicted, the integrated system optionally includes pipettor channel 120, e.g., protruding from body 102, for accessing a source of materials external to the microfluidic system. Typically, the external source is a microtiter dish or other convenient storage medium. For example, as depicted in FIG. 2, pipettor channel 120 can access microwell plate 208, which includes, e.g., sample materials, marker moieties, buffers, and the like, in the wells of the plate.

Detector 206 is in sensory communication with channel 104, detecting signals resulting, e.g., from fluorescent marker moieties. Detector 206 is optionally coupled to any of the channels or regions of the device where detection is desired. Detector 206 is operably linked to computer 204, which digitizes, stores, and manipulates and/or deconvolutes signal information detected by detector 206, e.g., using any of the instructions described above, e.g., or any other instruction set, e.g., for determining peak area, retention time, flow rate, molecular weight or identity. Computer 204 typically instructs fluid direction system 202 to change the pressure or voltage applied to a channel in response to information received from detector 206.

Fluid direction system 202 controls voltage, pressure, or both, e.g., at the wells of the systems or through the channels of the system, or at vacuum couplings fluidly coupled to main channel 104 or any other channel described above. Optionally, as depicted, computer 204 controls fluid direction system 202. In one set of embodiments, computer 204 uses signal information to select further parameters for the microfluidic system. For example, upon detecting a change in flow rate, the computer optionally directs the fluid direction system to alter the flow rate accordingly, e.g., to provide a substantially constant flow rate.

Kits

Generally, the microfluidic systems described herein are optionally packaged to include reagents for performing the device's preferred function. For example, the kits optionally include any of the microfluidic devices described herein along with assay components, reagents, sample materials, marker moieties, proteins, control materials, or the like. For example a protease inhibition assay kit typically includes a protease, a protease substrate, e.g., a protein, and a pair of marker moieties, e.g., rhodamine and flourescein, or any other combination of markers as described above. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device from a microwell plate). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits also optionally include packaging materials or containers for holding microfluidic device, system or reagent elements.

The discussion above is generally applicable to the aspects and embodiments of the invention described in the claims. Moreover, modifications can be made to the method and apparatus described herein without departing from the spirit and scope of the invention as claimed, and the invention can be put to a number of different uses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of monitoring a flow rate of a fluidic material in a microfluidic device, the method comprising:
    (i) flowing a first marker moiety through the-at least one microscale channel;
    (ii) flowing the fluidic material through the at least one microscale channel;
    (iii) flowing a second marker moiety through the at least one microscale channel;
    (iv) detecting the first marker moiety, resulting in detection of a first signal having, a first area and a first retention time;
    (v) detecting the second marker moiety, resulting in detection of a second signal having a second area and a second retention time; and,
    (vi) deconvoluting the first signal and the second signal to provide an indication of the flow rate of the fluidic material, wherein the deconvoluting comprises identifying differences in area and retention time between two or more of: the first signal, the second signal, a first selected standard, or a second selected standard.

2. The method of claim 1, wherein the deconvoluting step comprises comparing an area and a retention time of either the first selected standard or the second selected standard to one or more of: the first retention time and the first area, the second area and the second retention time, which first selected standard has a first selected area and a first selected retention time and, which second selected standard has a second selected area and a second selected retention time.

3. The method of claim 1, wherein deconvoluting comprises identifying or quantifying differences in area and retention time between two or more of: the first signal, the second signal, the first selected standard, or the second selected standard, which differences in area comprise differences in one or more of: height, width, area under curve, or width at half-maximum height.

4. The method of claim 1, wherein the first selected standard and second selected standard comprise initial assay conditions and deconvoluting comprises identifying and quantifying changes in the first and second signal from the initial assay conditions.

5. The method of claim 2, wherein comparing comprises identifying differences between one or more of: the first area and the first selected area, the second area and the second selected area, the first retention time and the first selected retention time, and the second retention time and the second selected retention time.

6. The method of claim 2, wherein the first selected retention time and the second selected retention time are different.

7. The method of claim 1, further comprising modulating the flow rate of the fluidic material, wherein the modulating comprises one or more of:
    (a) altering flow of the fluidic material through the at least one microscale channel;
    (b) altering flow of the first marker moiety through the at least one microscale channel; and,
    (c) altering flow of the second marker moiety through the at least one microscale channel.

8. The method of claim 1, further comprising altering the flow rate of the fluidic material into the at least one microscale channel in response to the indication of the flow rate provided by step (iv).

9. The method of claim 1, further comprising altering the flow rate of the fluidic material in the at least one microscale channel in the event that the first area and the second area are different.

10. The method of claim 9, further comprising increasing the flow rate in the event that the first area is larger than the second area.

11. The method of claim 9, further comprising decreasing the flow rate in the event that the first area is smaller than the second area.

12. The method of claim 8, further comprising increasing the flow rate in the event that the first area or the second area is smaller than a selected standard area.

13. The method of claim 8, further comprising decreasing the flow rate in the event that the first area or the second area is larger than a selected standard area.

14. The method of claim 8, further comprising changing the flow rate in the event that the first area and the second area have increased or decreased.

15. The method of claim 14, wherein deconvoluting comprises identifying a change in the ratio of one or more of: peak heights, peak widths, or peak areas, for the first signal and the second signal, thereby determining whether the flow rate has increased or decreased.

16. The method of claim 8, further comprising increasing the flow rate in the event that the first retention time or the second retention time is longer than a selected standard retention time.

17. The method of claim 8, further comprising decreasing the flow rate in the event that the first retention time or the second retention time is shorter than a selected standard retention time.

18. The method of claim 1, further comprising providing a microfluidic device, the device comprising:
    (a) a reaction channel; and, (b) a separation channel, which separation channel intersects the reaction channel.

19. The method of claim 18, comprising inducing flow of the fluidic material in the reaction channel by applying pressure to the reaction channel and electrokinetically inducing flow of the fluidic material in the separation channel.

20. The method of claim 19, wherein the first area and the second area provide an indication of the flow rate in the reaction channel and the first retention time and the second retention time provide an indication of the flow rate in the separation channel.

21. The method of claim 19, further comprising increasing the pressure applied in the reaction channel in the even that the first area or the second area decreases in comparison to a selected standard area.

22. The method of claim 19, further comprising decreasing the pressure applied in the reaction channel in the event that the first area or the second area increases in comparison to a selected standard area.

23. The method of claim 19, further comprising altering the pressure applied in the reaction channel in the event that the first area and the second area are different.

24. The method of claim 23, comprising increasing the pressure applied in the reaction channel in the event that the first area is larger than the second area.

25. The method of claim 23, comprising decreasing the pressure applied in the reaction channel in the event that the first area is smaller than the second area.

26. The method of claim 19, wherein electrokinetically inducing flow comprises applying a voltage gradient across the separation channel.

27. The method of claim 26, further comprising increasing the voltage applied across the separation channel in the event that the first retention time or the second retention time is longer that a first selected standard retention time or a second selected standard retention time.

28. The method of claim 26, further comprising decreasing the voltage applied across the separation channel in the event that the first retention time or the second retention time is shorter that a first selected standard retention time or a second standard retention time.

29. The method of claim 1, further comprising performing steps (ii), (iii) and (iv) such that the fluidic material is flowed after the first marker moiety and prior to the second marker moiety.

30. The method of claim 1, wherein the fluidic material comprises a label moiety.

31. The method of claim 30, wherein the label moiety is a fluorescent moiety.

32. The method of claim 1, wherein the first marker moiety is a non-reactive moiety.

33. The method of claim 1, wherein the first marker moiety comprises a label moiety.

34. The method of claim 33, wherein the label moiety is a fluorescent moiety.

35. The method of claim 1, wherein the second marker moiety is non-reactive moiety.

36. The method of claim 1, wherein the second marker moiety comprises a label moiety.

37. The method of claim 35, wherein the label moiety comprises a fluorescent moiety.

38. The method of claim 1, wherein the first marker moiety and the second marker moiety are the same.

39. The method of claim 1, wherein the first marker moiety and the second marker moiety are different.

40. The method of claim 39, wherein the first marker moiety and the second marker moiety have different electrophoretic mobilities.

41. The method of claim 39, wherein the first retention time and the second retention time are different.

42. The method of claim 40, wherein the first marker moiety is neutral and the second marker moiety is charged.

43. The method of claim 40, wherein the first marker moiety is charged and the second marker moiety is neutral.

44. The method of claim 1, wherein the first marker moiety and the second marker moiety comprise a first fluorescent moiety and a second fluorescent moiety.

45. The method of claim 44, wherein detecting comprises fluorescently detecting the first fluorescent moiety and the second fluorescent moiety.

46. The method of claim 1, further comprising detecting the fluidic material, the first marker moiety and the second marker moiety with a single detector.

47. The method of claim 1, the method further comprising detecting the fluidic material, resulting in detection of at least a third signal.

48. The method of claim 1, further comprising iteratively repeating one or more of: steps (i) through (vi).

49. The method of claim 1, further comprising providing a fluid direction system operably coupled to the microfluidic device, which fluid direction system directs one or more of:
   (a) flow of the fluidic material through the at least one microscale channel;
   (b) flow of the first marker moiety through the at least one microscale channel; and,
   (c) flow of the second marker moiety through the at least one microscale channel.

50. The method of claim 49, further comprising providing a detection system, which detection system comprises a detector that detects one or more of: the first signal and the second signal.

51. The method of claim 50, further comprising providing a computer, operable coupled to the detection system and the fluid direction system, the computer comprising software, which software comprises at least a first instruction set, which first instruction set instructs the fluid direction system to modulate the flow rate of the fluidic material in response to one or more of: the first signal and the second signal detected by the detection system.

52. The method of claim 51, wherein the first instruction set deconvolutes one or more of: the first signal and the second signal, to provide an indication of the flow rate of the fluidic material.

53. The method of claim 50, wherein the first instruction set determines a difference between one or more of: a first selected standard and the first signal, a second selected standard and the second signal, and the first signal and the second signal and instructs the fluid direction system to modulate the flow of the fluidic material in the at least one microscale channel based on the difference.

54. The method of claim 50, wherein the software comprises a second instruction set, which second instructions et calculates the flow rate of the fluidic material.

55. The method of claim 1, further comprising:
   (vii) providing a pressure source and a sample source, which pressure source is fluidly coupled to the microfluidic device, and
   (viii) introducing the fluidic material into the microfluidic device from the sample source by drawing fluid from the sample source into the microfluidic device by applying pressure from the pressure source.

56. The method of claim 55, wherein the pressure source comprises a siphone, a vacuum source, a programmable syringe pump, or an electroosmotic pump, which siphon, vacuum source, programmable syringe pump, or electroosmotic pump introduces the fluidic material into the microfluidic device from the sample source.

57. The method of claim 55, wherein the sample source comprises a plurality of sample sources and a plurality of marker sources.

58. The method of claim 57, wherein the sample source further comprises a plurality of buffer sources.

59. The method of claim 57, further comprising introducing the first marker moiety, the second marker moiety, or the first marker moiety and the second marker moiety, from the sample source into the microfluidic device after introducing the fluidic material.

60. The method of claim 57, further comprising introducing the first marker moiety into the microfluidic device before introducing the fluidic material and introducing the second marker moiety into the microfluidic device after introducing the fluidic material.

61. The method of claim 57, further comprising introducing a plurality of fluidic materials from the sample source into the at least one microscale channel.

62. The method of claim 61, wherein the plurality of fluidic materials comprises about 96 or more, about 384 or more, or about 1536 or more different fluidic materials.

63. The method of claim 61, further comprising introducing the first marker moiety, the second marker moiety, or the first marker moiety and the second marker moiety, into the at least one microscale channel from the sample source after introducing each member of the plurality of fluidic materials.

64. The method of claim 61, further comprising introducing the first marker moiety prior to introducing each member of the plurality of fluidic materials and introducing the second marker moiety after introducing each member of the plurality of fluidic materials.

65. The method of claim 62, further comprising introducing the first marker moiety, the second marker moiety, or the first marker moiety and the second marker moiety into the at least one microscale channel from the sample source after introducing about five or more members of the plurality of fluidic materials into the at least one microscale channel.

66. The method of claim 62, further comprising introducing the first marker moiety prior to introducing about five or more members of the plurality of fluidic materials and introducing the second marker moiety after introducing about five or more members of the plurality of fluidic materials into the at least one microscale channel.

67. The method of claim 62, further comprising introducing the first marker moiety, the second marker moiety, or the first marker moiety and the second marker moiety into the at least one microscale channel from the sample source after introducing about ten or more members of the plurality of fluidic materials into the at least one microscale channel.

68. The method of claim 62, further comprising introducing the first marker moiety prior to introducing about ten or more members of the plurality of fluidic materials and introducing the second marker moiety after introducing about ten or more member of the plurality of fluidic materials into the at least one microscale channel.

69. The method of claim 62, further comprising introducing the first marker moiety, the second marker moiety, or the first marker moiety and the second marker moiety into the at least one microscale channel from the sample source after introducing about twenty or more members of the plurality of fluidic materials into the at least one microscale channel.

70. The method of claim 62, further comprising introducing the first marker moiety prior to introducing about twenty or more members of the plurality of fluidic materials and introducing the second marker moiety after introducing about twenty or more members of the plurality of fluidic materials into the at least one microscale channel.

* * * * *